United States Patent [19]

Kranys et al.

[11] 4,006,736

[45] Feb. 8, 1977

[54] ANGIOGRAPHIC INJECTOR

[75] Inventors: Rudolph J. Kranys, Allison Park; Marlin S. Heilman, Gibsonia; Ronald J. Zdrojkowski; George R. Swann, both of Pittsburgh, all of Pa.

[73] Assignee: Medrad, Inc., Pittsburgh, Pa.

[22] Filed: Nov. 27, 1974

[21] Appl. No.: 527,520

[52] U.S. Cl. .................. 128/2 A; 128/DIG. 1; 128/218 A

[51] Int. Cl.² ............. A61B 6/00; A61M 5/20

[58] Field of Search .......... 128/2 A, 2 R, DIG. 1, 128/DIG. 13, 218 A

[56] References Cited

UNITED STATES PATENTS

| | | | |
|---|---|---|---|
| 2,734,504 | 2/1956 | Crescas et al. | 128/218 A |
| 2,764,980 | 10/1956 | Smith | 128/218 A |
| 3,297,210 | 1/1967 | Lucas | 128/DIG. 1 UX |
| 3,344,275 | 9/1967 | Marchal et al. | 128/2 A UX |
| 3,623,474 | 11/1971 | Heilman et al. | 128/2 R |
| 3,631,847 | 1/1972 | Hobbs | 128/2 R |
| 3,701,345 | 10/1972 | Heilman et al. | 128/2 R |
| 3,718,138 | 2/1973 | Alexandrov et al. | 128/DIG. 1 |
| 3,812,843 | 5/1974 | Wootten et al. | 128/2 R |
| 3,888,239 | 6/1975 | Rubinstein | 128/2 A |

*Primary Examiner*—Kyle L. Howell
*Attorney, Agent, or Firm*—Fleit & Jacobson

[57] ABSTRACT

An apparatus for injecting fluid, specifically contrast media, into the vascular system of a human being or other animal. The apparatus comprises a head portion and a control unit. The head portion includes the motor and drive components, and carries a removable syringe cartridge containing the fluid. Integral with the head portion is a pressure jacket for housing the syringe cartridge, and a piston plunger for forcing the fluid out of the syringe cartridge, through a catheter and into the vascular system. The control unit includes the mechanism for selecting delivery parameters, and circuitry for controlling the delivery of the contrast media into the vascular system. Also disclosed is a syringe cartridge designed to cooperate with the apparatus for injecting contrast media.

31 Claims, 29 Drawing Figures

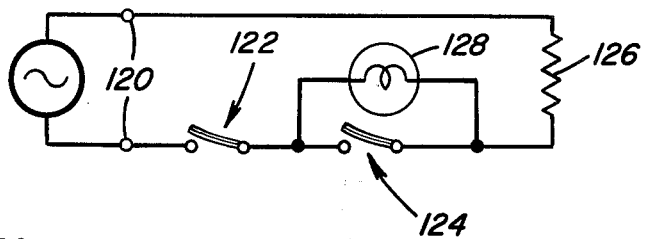
FIG. 7
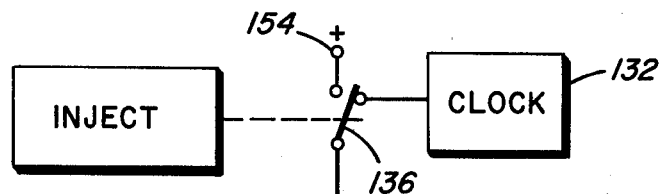
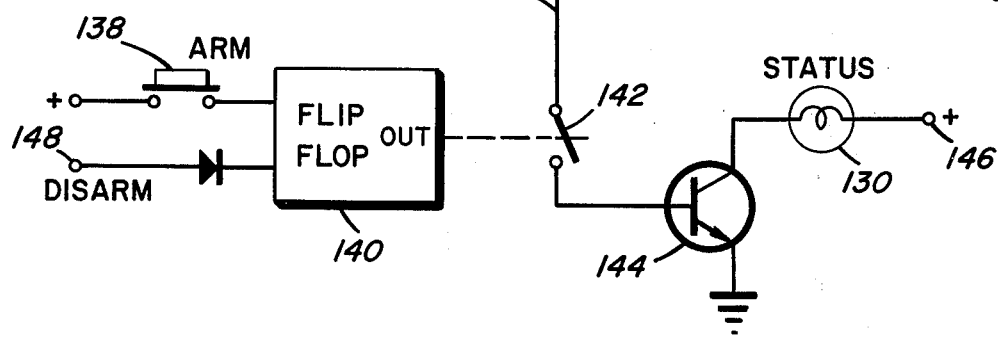
FIG. 8
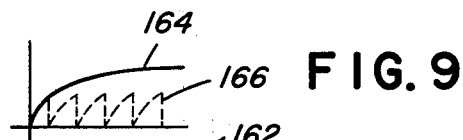
FIG. 9
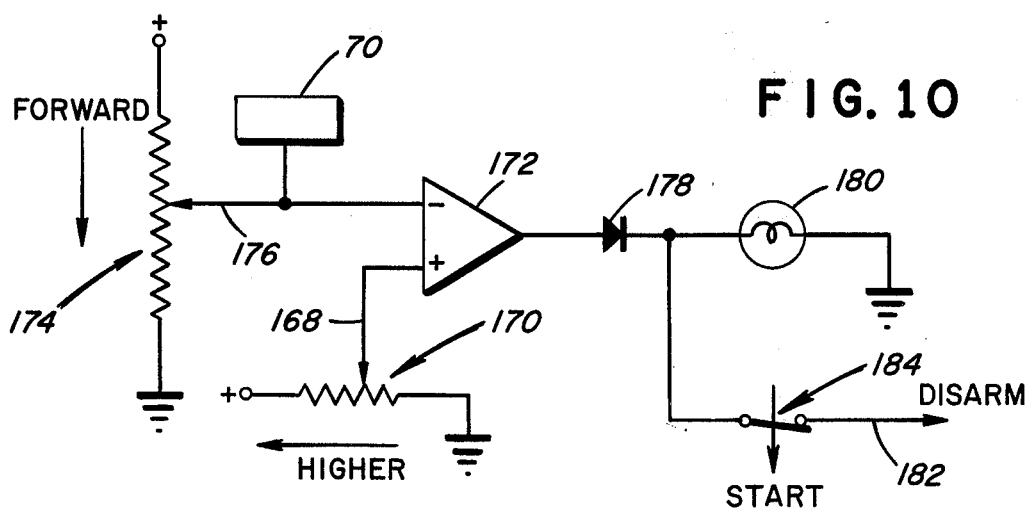
FIG. 10

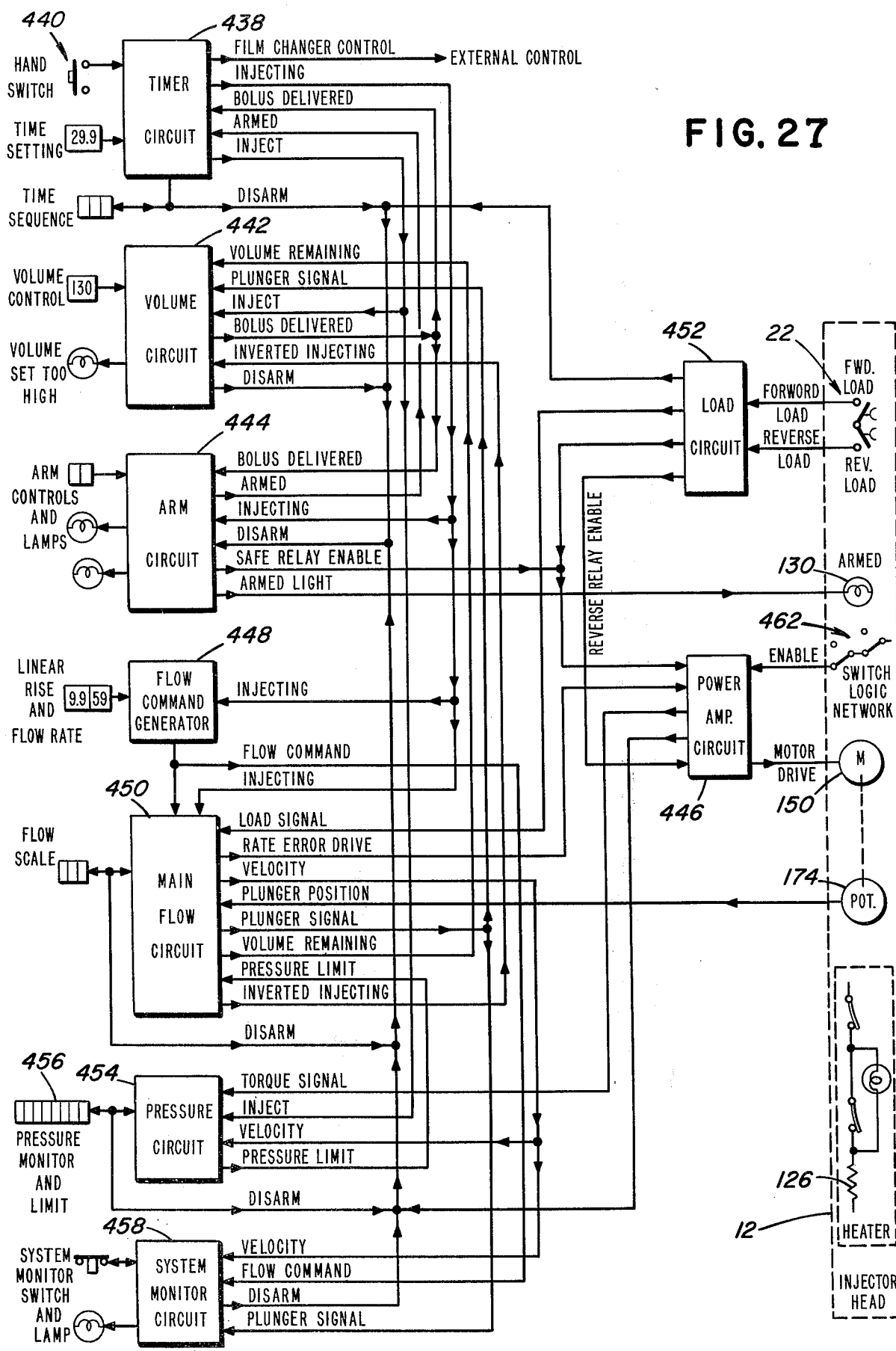

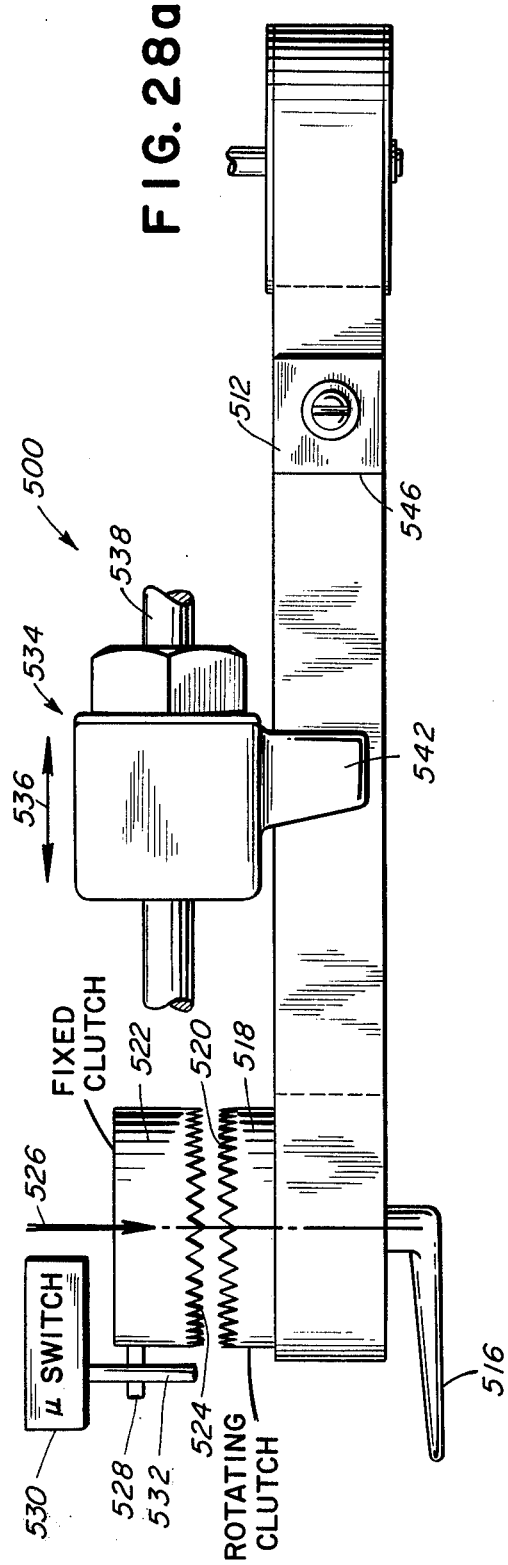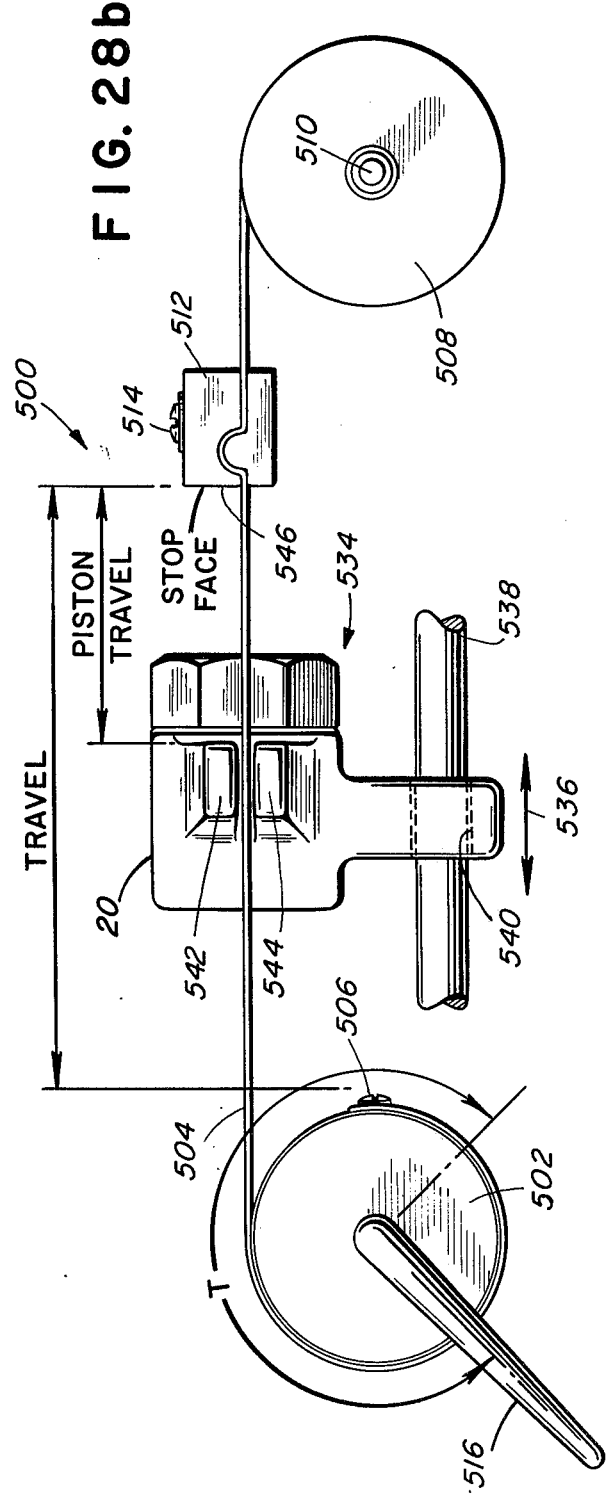

ANGIOGRAPHIC INJECTOR

BACKGROUND OF THE INVENTION

This invention pertains to the field of angiography. Angiography is the study of blood vessels with the use of x-rays while injecting an iodine-based or other fluid (contrast media) into the body through a catheter situated in a blood vessel. An angiographic injector is an apparatus which controls the delivery rate, amount, and maximum pressure of the fluid being injected.

There are many angiographic injectors on the market today, and each suffers from its own characteristic drawbacks and deficiencies. A few are noted in the paragraphs to follow.

A bothersome and time-consuming operation necessary in the use of all known injectors is that of exchanging an empty syringe cartridge with a filled one. Known injectors necessitate a certain degree of mechanical disassembly, be it unscrewing a collar, turning a handle to remove a subassembly, or a similar maneuver to gain access to the empty syringe cartridge. Once a fresh cartridge is in position, the reverse operation of mechanical assembly must be carried out before the injector is ready for another injection.

It is known to elevate the temperature of the contrast media to that of the body prior to injection. It is also known that if the contrast media is injected at a temperature above approximately 106° F, damage to the brain may occur. Though attempts have been made to ensure that the temperature of the contrast media is maintained below the critical 106° F, none has been totally satisfactory.

Known angiographic equipment have incorporated indicators to show when the injector is ready to inject. The indicators, however, maintain the same state for readiness and injection. Therefore, while the operator is readily able to discriminate between disarmed and readiness, it is difficult to discriminate between readiness and injection.

Another drawback of prior equipment relates to the controls for filling syringes by using the injector. Such controls traditionally drive the plunger of the injector at a constant rate, and hence the filling operation cannot be conducted at maximum efficiency.

The volume of contrast media to be delivered depends upon settings manually introduced to the apparatus. With a single injection, the syringe is filled to the volume required, or higher, and the volume control is set to the desired volume of injection. However, if several injections are to be made from the same syringe, the amount of fluid remaining in the syringe for any given injection may be less than that required for injection. Such a condition of insufficient syringe volume cannot be detected in known angiographic injectors.

Known flow controlled injectors using servo feedback systems, adjust the injection pressure to deliver the contrast media at the desired and set injection rate. Occasionally there may be insufficient pressure, resulting in an underrate injection. Such an underrate injection will go unnoticed in injectors on the market today.

Several injectors available today are equipped with a mechanism for controlling equipment auxiliary to the injector system, particularly film changers or film changer programmers used in conjunction with the injector system. Typically, a film sequence is initiated by a switch closure in the injector itself, completing a circuit within the auxiliary equipment. Though it is desireable to synchronize the changing of the film in the film changer with the injection contrast media into the vascular system, there are no effective R-wave synchronism capabilities in presently available angiographic injectors.

Also important is that the operator be capable of accurately planning an injection sequence. And since cardiac injections are customarily carried out in pulses, spaced so as to synchronize with the ECG, it would be helpful for the operator to have a visual display of the patient's cardiac activity. Yet no known injectors provide a mechanism for displaying the pertinent cardiac activity to enable the operator to accurately map out an injection program.

Nor does any known angiographic injector have the ability to preview injection parameters displayed with respect to the ECG. That is, there is no present capability for visually inspecting the pre-set injection parameters prior to an actual injection in order to determine if all parameters are properly set. Similarly, there are no known injectors which visually display the entire injection sequence as it was actually carried out.

An important drawback of today's injectors is that a high-pressure injection can be initiated prior to the completion of the entry of injection parameters, or in the event that a parameter has been inadvertently changed. There are some safety features on known equipment, but none sophisticated enough to ensure a high degree of safety.

Conventional motor systems for controlling the injection of contrast media have been plagued by runaway or burned motors, or other similar detrimental failures in the motor control system. Numerous safety features, including fuses, circuit breakers, brakes, crowbar circuits, current limiting circuits, and over-current detecting circuits have been incorporated. But the known injectors have still failed to provide inherent safety from the types of failures described above.

The flow of blood varies in different portions of the body and even in different portions of the heart cycle. This creates a problem in angiography, because vessel opacification is a function not only of injection rate, but also of blood flow rate. Accordingly, there is a need to have the capability of programming variable injection rates in an angiographic injector. In this regard, U.S. Pat. No. 3,812,843 describes stepping to new injection rate values in a time sequence in order to build a programmed injection function. However, only this stepped sequence is disclosed in the programming of variable injection flow rates.

Another serious problem in conventional angiographic equipment relates to the injection of air into the vascular system. There have already been deaths caused by the initiation of injections with empty syringes. A need obviously exists for a mechanism whereby the presence of an empty or an only partially filled syringe can be detected prior to injection.

There is also the need in angiography for improvements in both disposable and media-containing syringe cartridges. In particular, today's syringes suffer from serious drawbacks with respect to sterility. They are frequently not pre-sterilized to satisfaction prior to an injection. A need also exists for syringe cartridges which may readily be associated with an angiographic injector without unduly stressing the injector or the cartridge itself.

Especially common with respect to disposable syringe cartridges is the problem of syringe capacity changes which result during high-pressure injections. When the cartridge assembly is subjected to the injection pressures, the cartridge swells and hence the initial injection rate is decreased. Similarly, when the injection pressure is reduced at the end of the injection, the cartridge deflates, and hence injection of contrast media continues when none is desired. No known injectors in any way compensate for this change of syringe capacity due to the application of injection pressures.

Other problems and drawbacks are common to the angiographic injectors known today. Among these are the complexity of the apparatus necessary to develop electrical indications of parameters such as the actual pressure developed at the tip of the syringe during an injection, and the difficulty encountered by servicemen in pinpointing the location of problems should they occur in the equipment. Furthermore, known angiographic injectors are generally lacking in the capability of being remotely controlled, and employ panel elements which are susceptible to the accumulation of fluids and dust.

It is the purpose of the present invention to cure each of the drawbacks and disadvantages of known angiographic injectors discussed in the preceding paragraphs.

SUMMARY OF THE INVENTION

The present invention relates to an advanced angiographic injector for delivering contrast media to the vascular system of a patient. The inventive injector is generally simple in design, and yet eliminates or cures ills which have long been common in the field of angiography.

The inventive angiographic injector has a head portion which employs a rotating turret arrangement for housing two syringe cartridges at the same time. When one syringe is in operative alignment with the piston drive, the other is maintained in a state of readiness. Then, when the first syringe is either or has less contrast media than is called for in the ensuing injection, the new filled syringe is exchanged for the other by simply turning the turret 180°. A safety mechanism is also provided to ensure proper alignment of the syringe prior to the initiation of an injection, as is a strong and reliable clip for accepting and controlling the plunger of the syringe, and for accomodating syringes received from either of two directions of turret rotation.

The inventive injector is also equipped with an apparatus which snaps around the pressure jackets of the two syringe cartridges housed in the rotating turret to elevate the temperature of the contrast media to that of the body prior to injection. Unlike known heating elements previously used, the inventive heater has automatic and redundant temperature control circuitry, and also includes a visual indication of failure in the primary temperature sensor.

The inventive injector is also equipped with indicators to show when the injector is not in readiness for injection, when it is ready to inject, and when the injection is in progress. A single indicator identifies three states, off when disarmed (unable to inject), flashing when armed (ready to inject), and on full when injecting.

The loading controls on the present injector incorporate pre-programmed rate changes for optimum air expulsion during the filling operation. In particular, loading is controlled by a single switch on the injector head and its associated circuitry. By pulsing the switch, the piston maintains a slow speed. However, if the switch is held, the piston speed increases with the passage of time.

The inventive injector also overcomes the problem of the operator calling for more contrast media than that housed in the syringe. The present injector has an indicator which shows when the desired injection volume exceeds the actual syringe volume. The injection is prevented under this circumstance. The operator, generally standing in front of the control unit and remote from the injector head, can also use this feature to determine the amount of contrast media actually remaining in the syringe.

The injector described herein is also equipped with a mechanism for protecting against underrate injections due to insufficient pressure. An indication is given, of either the actual rate developed or the error between the actual rate and the desired injection rate. A meter is provided which reads and stores the highest actual flow rate attained by the injector. At the same time, pressure lamps are illuminated and so maintained, indicating the actual pressure attained. In this manner, the operator is given the option to stop the injection if it is sufficiently underrate.

Also provided is a unique manner of controlling equipment auxiliary to the injector, such as a film changer. The present injector incorporates circuitry for synchronizing the signal which triggers the film changer to the ECG. The trigger may be initiated on the R-wave, or delayed for an adjustable time until after the R-wave has passed. The trigger signal follows a square waveform, is initiated by the ECG and has an adjustable duty time period (switch closed). The trigger may therefore be used to respond to one R-wave and remain closed, or to respond to several R-waves, staying closed only for a short adjustable period after each R-wave. By so synchronizing with the R-waves, it is ensured that the film changer is always triggered when desired, even if there is a dramatic change in the heart rate.

The injector of the present invention incorporates a mechanism for displaying the time period between R-waves on a beat-to-beat basis. Such information enables the operator to select a program which will be confined to the R-to-R interval. Specifically, the injector displays time in hundreths of a second between successive R-waves. Therefore, if the operator desires a 0.5 sec. injection program, wants a period of 0.1 sec. after the conclusion of the injection and prior to the next R-wave, and wishes to delay the film changer after the beginning of the R-wave, he knows that he has a maximum of 0.2 sec. in which to program a delay, if the R-to-R interval is 0.8 sec.

The ability to preview injection parameters displayed with respect to the ECG, is also to be found in the inventive injector described herein. The flow and volume parameters set by the operator may be displayed on a self-contained oscilloscope, or may be fed out to auxiliary equipment for monitoring or recording. If displayed, these parameters will be seen in their proper time relationship, and will be synchronized to the ECG in order to determine if all parameters are properly set. Any adjustments can then be made prior to the initiation of the injection. The same oscilloscope which provides a preview of the set injection program can be utilized to recall the entire actual injection sequence. In this mode, the oscilloscope memory is automatically initiated just prior to an injection and is automatically disabled after the conclusion of the injection.

A safety feature utilized in the present injector prevents the initiation of an injection should an important injection parameter not be set, or, if a parameter has been changed, perhaps due to inadvertence. Certain of the pertinent variables must be selected before an injection can begin. Failure to select one of these variables, or changing certain control functions once selected, will automatically disarm the injector.

The inventive injector utilizes a motor power control circuit of such design as to be inherently safe. Without any additional protective means, such as those commonly found in the prior art, failure of the motor control output circuit causes the motor to stop. Thus regardless of failure mode, power is interrupted. In particular, the drive motors are powered through transformers, with motor speed control being in the form of pulse-width modulated signals.

The present invention includes circuitry for carrying out two novel approaches to programming variable injection flow rates. The first approach is a four-mode injection rate program where a number of the modes may be optionally deleted. The first mode is a linear acceleration of injection rate from zero ml/sec to a set rate level, the acceleration to occur in a set time. The next mode is the maintenance of the achieved flow level for a set time or volume. Thirdly, there is the acceleration or deceleration to a new level of injection rate, the rate change to occur as set. The fourth mode is the maintenance of the second injection rate level for a set volume. The second approach to variable rate control is a succession of increasing or decreasing bolus injection rates, each bolus being triggered by and in time relationship with the pulses of a train of ECG R-waves. This latter approach is useful in determining the flow rate of blood in a vessel. By incrementally increasing the delivered injection rate, actual blood flow rate will occur when backflow is developed.

The present invention further relates to an angiographic injector in which the risks of injecting air into the vascular system are minimized. With the entire volume of a syringe (between plunger and tip of syringe) filled with contrast media, there will be only minimal compression of the fluid during a high-pressure injection. With an empty syringe, or one in which air bubbles are present, the air will compress to a considerable extent under injection pressures. This compression will be reflected in the current draw of the driving motor. The inventive injector is equipped with a mechanism which indicates low-current demands from the driving motor, indicative of air in the syringe. An even more accurate air indication signal may be derived by dividing the pressure signal by the actual injection rate signal to achieve a signal roughly proportional to the impedance seen by the plunger. With air in the syringe, this impedance signal will be unusually low.

The present invention also relates to a syringe cartridge adapted for use with the disclosed angiographic injector. The syringe cartridge is equipped with a double seal between the plunger and syringe body to ensure strength at pressures on the order of 1200 to 2000 psi. During gas sterilization, gas is permitted to enter the space between the two plunger seals through surface irregularities in the form of ribs in the rear portion of the syringe body. In addition, the syringe plunger associates with a driving mechanism in the injector head through a button extension on the outside of the plunger. The button extension is designed so as to minimize stress in the driving mechanism of the injector head and the button and its stem, and to facilitate connection between the button and drive.

The inventive injector is also provided with a feedback circuit which increases the injection rate at the beginning of a high-pressure injection, and decreases the injection rate at the end of an injection. In this manner, the changes in syringe capacity due to pressure stresses are automatically compensated for, thereby sharpening both the rise time and fall time of a typical injection cycle.

Other provisions made in the inventive angiographic injector include a direct read-out of the actual pressure developed at the tip of the syringe and a full set of indicator lamps which selectively illuminate upon failure of respective injector circuits and components, thereby facilitating the task of a serviceman. All of the injection parameters can be controlled external to the injector, by remotely developed control signals, or by capacitance-type switches on the control unit, impervious to spillage of contrast media or other contaminants.

It is therefore the object of the present invention to provide an angiographic injector and a syringe cartridge for use therewith, which avoid or eliminate the drawbacks of known angiographic injectors discussed above.

This and other objects of the present invention will become more clear when specific reference is made to the following description, taken in conjunction with the accompanying drawings.

BRIEF DESCRIPTION OF THE DRAWINGS

FIG. 7 is a circuit schematic of the media heater employed in the present invention;

FIG. 8 is a schematic representation of the status indicating circuit employed in the inventive injector;

FIG. 9 is a schematic of the inventive load control circuit;

FIG. 10 is a schematic of the inventive volume indicator circuit;

FIG. 27 is an overall block diagram illustrating the circuitry employed in the inventive injector.

FIG. 28a is a top view of a mechanism for preventing excessive travel of the plunger used in the inventive angiographic injector; and FIG. 28b is a side view of the mechanism illustrated in FIG. 28a.

DETAILED DESCRIPTION OF THE DRAWINGS

Figure 1:
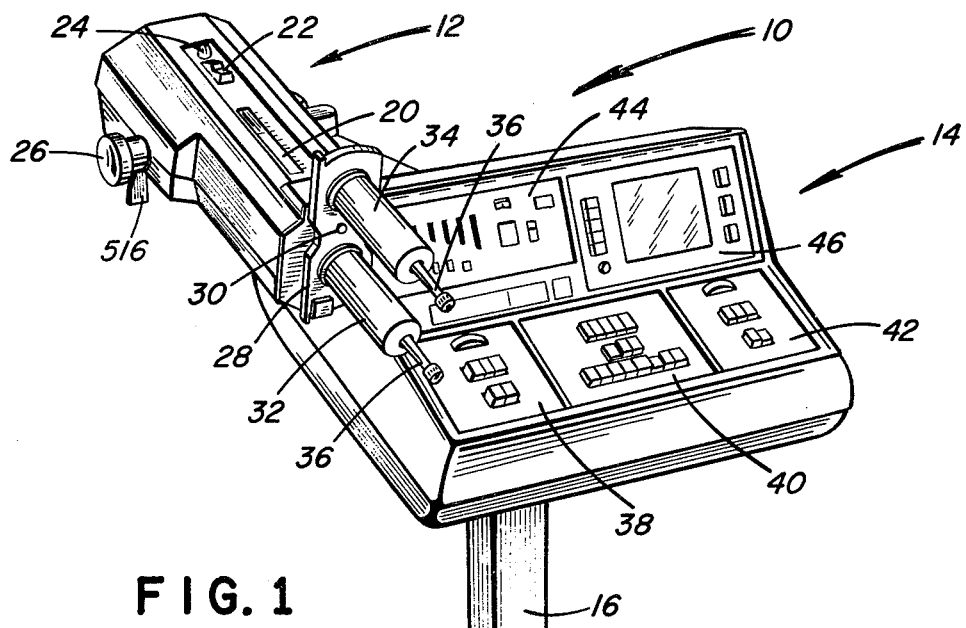
FIG. 1 is a perspective view of the inventive angiographic injector, illustrating the head portion and the control unit.

With reference first to FIG. 1, the inventive angiographic injector is shown generally at 10. The injector 10 comprises a head portion 12, a control unit 14 and a stand 16 which is movable on wheels 18. On the top of the head portion 12 is a scale 20, a control button 22 and an indicator lamp 24. A knob 26 and a lever 5/6 are provided for manual operation of the head portion 12.

On the forward portion of head 12 is a turret 28 rotatably mounted about a bolt 30. Two pressure jackets 32 and 34 are fixed in turret 28, and house respective syringe cartridges, only the tips of which can be seen at 36.

The panel of the control unit 14 illustrated in FIG. 1 is divided into five discrete regions, each of which has its own controls. The numeral 38 refers to a volume module, the numeral 40 to a flow module and 42 to a timer module. Indicated at 44 is a variable flow rate control module, and an oscilloscope module is shown at 46.

With reference to FIGS. 2 through 6, the two-syringe turret mechanism will be described. As seen best in FIGS. 2 and 6, the turret 28 is equipped with two projecting stops 50 and 52, respectively. Fixed to the injector head 12, and adapted to associate with the stops 50 and 52 on the turret 28, are abutment members 54 and 56, respectively. The association between the stops 50 and 52 and the abutment members 54 and 56 limits the rotation of the turret 28 from the position illustrated in FIG. 2 to the position illustrated in FIG. 6. That is, with respect to FIG. 6, the turret 28 can turn only in the direction of arrow 58. Once in the position shown in FIG. 2, the turret can turn only in the direction of arrow 59.

Figure 2:
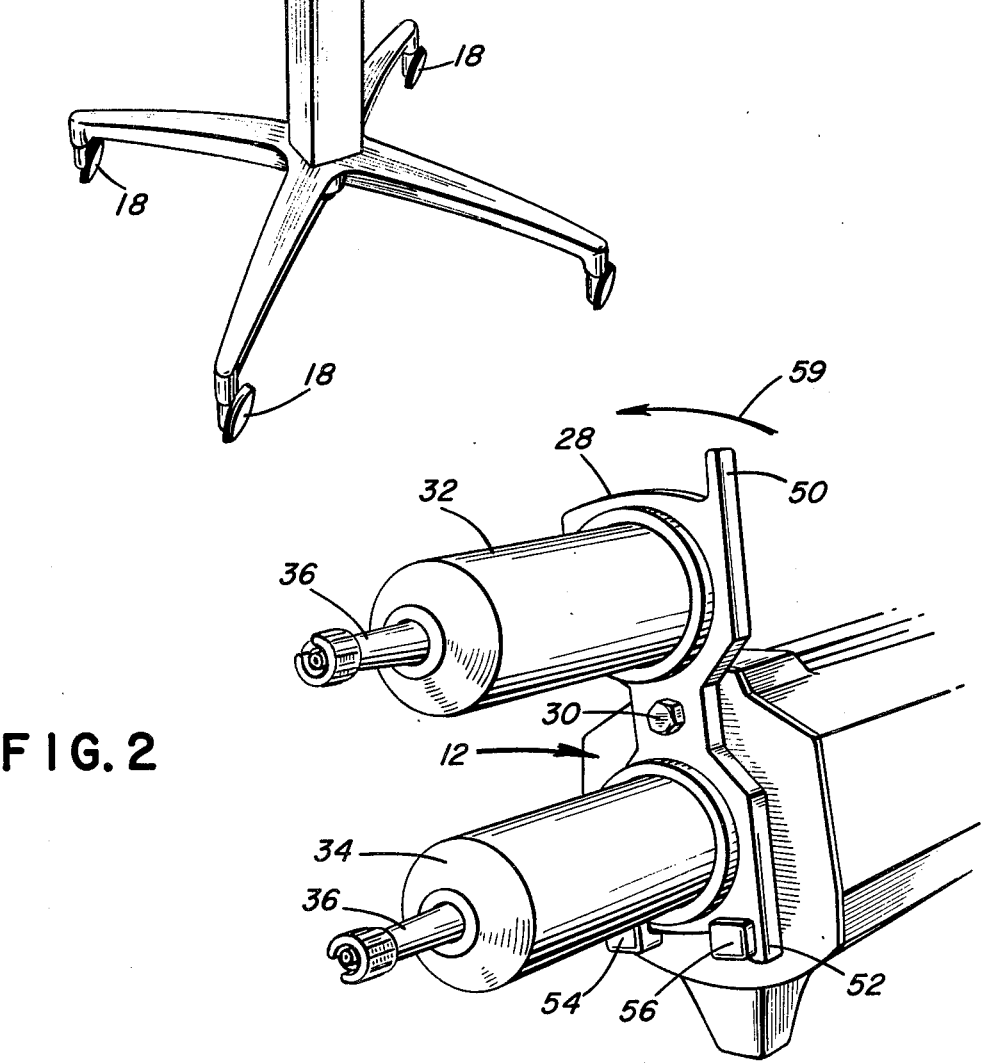
FIG. 2 is a front perspective view of the two-syringe turret assembly of the inventive injector, with one syringe in a position ready for an injection.
Figure 3:
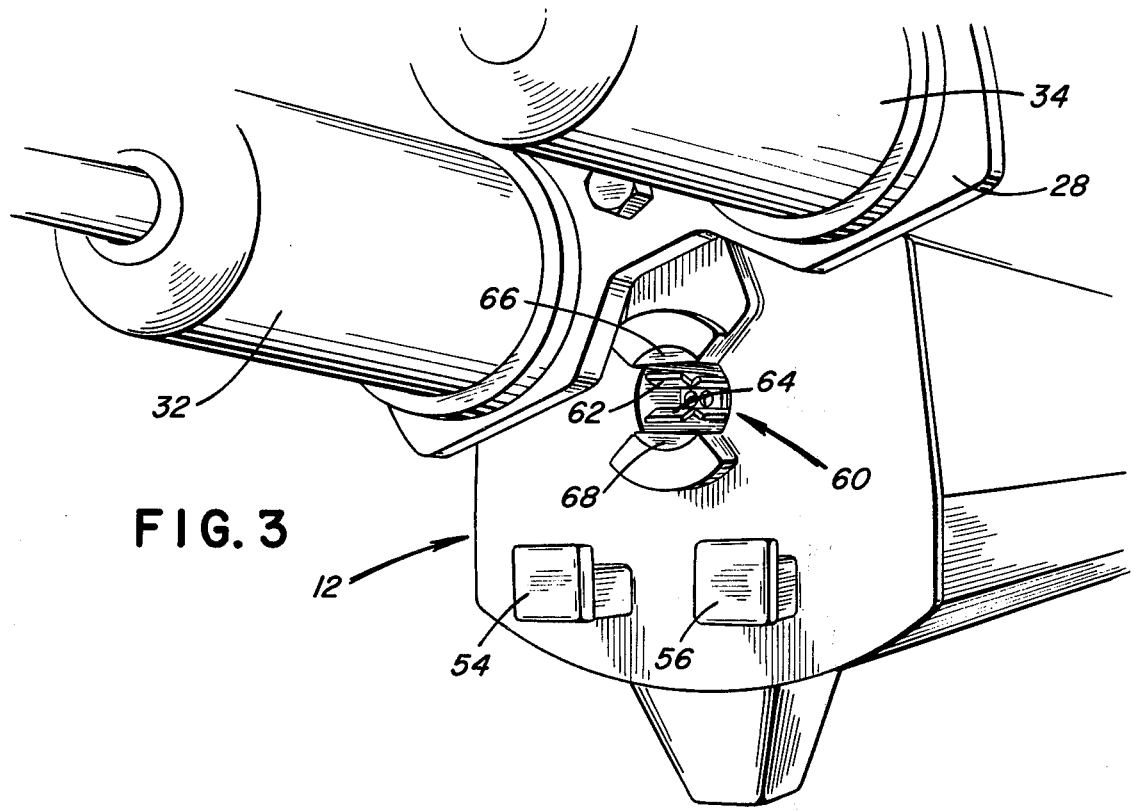
FIG. 3 is a view similar to FIG. 2, but illustrating the turret rotated out of operative position to expose the plunger-engaging driving mechanism of the head portion.
Figure 4:
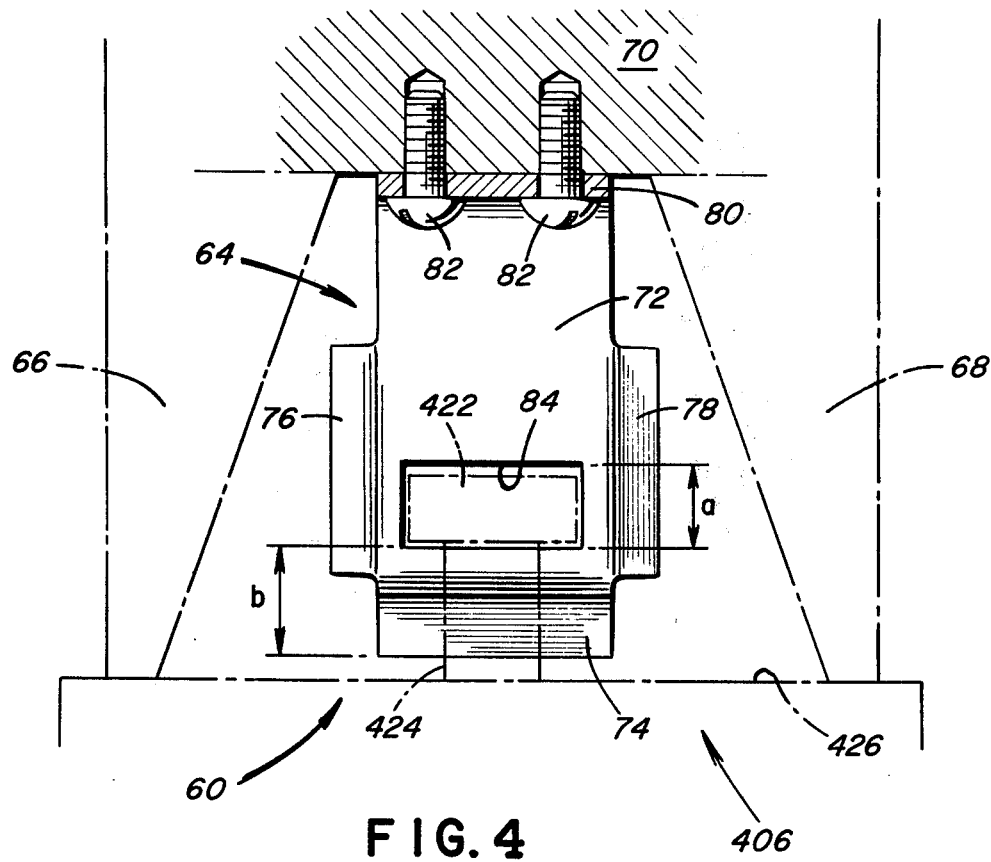
FIG. 4 is a plan view of one of the two clips in the driving mechanism illustrated in FIG. 3.
Figure 6:
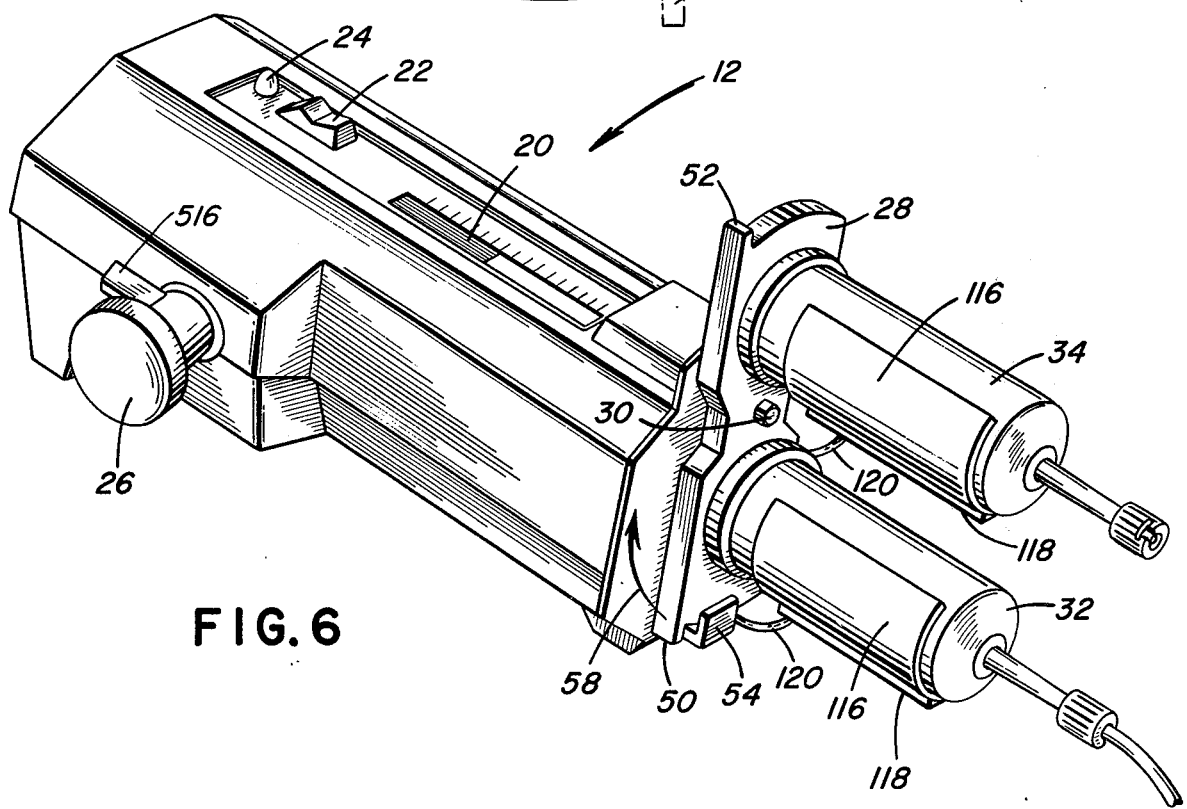
FIG. 6 is an enlarged side perspective view of the head portion of the inventive injector.

FIG. 3 illustrates a position of the turret 28 intermediate those illustrated in FIGS. 2 and 6. In this position, the driving mechanism shown generally at 60 is exposed. Driving mechanism 60 includes a pair of resilient independently suspended clips 62 and 64, and a pair of integral rams 66 and 68. It should be noted that the rams 66 and 68 have been rotated 90° in FIG. 4 to facilitate description. As can be seen in FIG. 4, the ram elements 66 and 68 are integral with and extend from a main plunger surface 70. As will be described in greater detail below, the plunger 70 is motor driven by a mechanism mounted in the head portion 12.

Clips 62 and 64 are of similar design, and hence only clip 64 is illustrated in FIG. 4. As can be seen, resilient clip 64 has a main planar body 72, a downwardly projecting front face 74, and downwardly projecting side faces 76 and 78, respectively. A rear flange 80 of the clip 64 serves as a mounting plate through which the clip is fixed to the plunger 70 by a pair of bolts 82. A rectangular opening 84 is cut through the planar surface 72 of clip 64.

Clip 62, as best seen in FIG. 3, is of similar design but inverted with respect to clip 64. The cooperation between clips 62 and 64 will be explained in the following paragraphs. For reasons which will also be explained below, the dimensions $a$ and $b$ represented in FIG. 4 are critical relative to the dimensions of the associating syringe. In this regard, the clip dimension $a$ is on the order of 0.155 inches. The dimension $b$ is somewhere between 0.19 and 0.20 inches.

Figure 5:
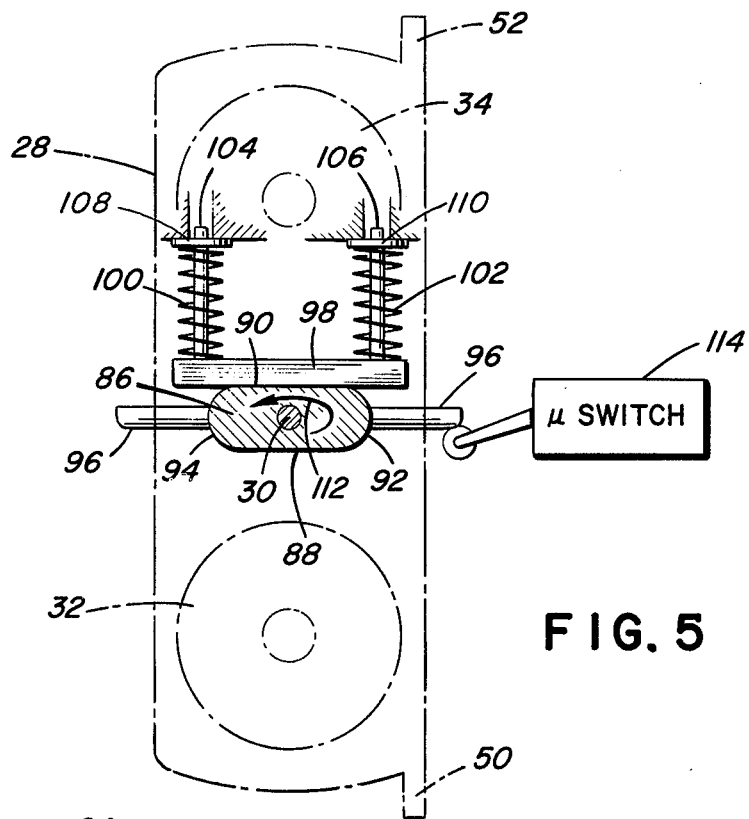
FIG. 5 is a schematic representation of the turret alignment mechanism.

FIG. 5 illustrates the centering mechanism associated with the rotatable turret 28. Integral with the side of the turret 28 remote from the head of bolt 30 is a flattened extension 86. Extension 86 is elongated in the direction of bolt 30, and is provided with two flat faces 88 and 90, and two rounded faces 92 and 94, respectively. A pin 96 is fixed on each rounded face 92 and 94, and hence the respective pins turn with the extension 86 about bolt 30.

A flat plate 98 offset with respect to the pins 96 is urged against extension 86 by means of springs 100 and 102. The springs 100 and 102 are mounted on rods 104 and 106, and are retained by washers 108 and 110, respectively. Washers 108 and 110 are fixed relative to the housing of head portion 12.

Upon rotation of the turret 28, the rear extension 86 also rotates. The turret 28 is rotated by hand, and the springs 100 and 102 are relatively weak, so that only minimum resistance to rotation is encountered. When the extension 86 rotates about bolt 30, the plate 98 is cammed upwardly and toward washers 108 and 110. The plate 98 reaches its highest point when in contact with rounded faces 92 and 94, and always is urged toward extension 86. Accordingly, should extension 86 be rotated in the direction of arrow 112, the plate 98 will be cammed away from surface 90, in contact with surface 92, and ultimately with surface 88. When the surface 88 is nearly planar with plate 98, the force exerted by springs 100 and 102 urges extension 86 into a position whereby intimate contact is made between flat face 88 and plate 98.

With either of the two faces 88 or 90 in intimate contact with plate 98, one of the two syringes carried by the turret 28 is in a position ready for injection. A microswitch 114 associates with the pins 96, and closes a circuit which enables an injection operation. The stops 50 and 52 associate with the abutments 54 and 56 very near the position of the turret 28 in which one of the flat faces 88 or 90 is in contact with plate 98.

With reference now to FIGS. 6 and 7, the inventive temperature control mechanism will be described. In FIG. 6, there is illustrated a heater sleeve 116 mounted on each of the respective pressure jackets 32 and 34. Heater sleeves 116 are of a resilient material, are adapted to hug the respective pressure jackets, and have heater elements imbedded therein. As illustrated, the sleeves 116 are open at the top and have an enlarged casing 118 at the bottom to house the electronics. Electrical leads 120 carry energy to the circuitry in the heater sleeves 116. With reference to FIG. 7, the circuitry housed in portion 118 of heater sleeve 116 will be described. An alternating current signal is delivered to the heater circuitry via leads 120. Two normally closed bimetallic thermostats 122 and 124, respectively, normally close the circuit between the source of current and a heater element indicated by resistor 126. Thermostat 122 is designed to open at 98° F, and thermostat 124 is designed to open at 108° F. A lamp 128 is connected in parallel to the thermostat 124. And while not illustrated, lamps 128 are adapted to shine into the respective pressure jackets 32 and 34 through an opening in the inside of portion 118.

Under normal operating conditions, the circuit will be closed between the current source, thermostats 122 and 124, and the heater element 126. When a temperature of 98° F is obtained, thermostat 122 will open and interrupt the delivery of current to heater element 126. Then, when thermostat 122 cools, it will again close, and again heater element 126 will be energized. If thermostat 122 should fail, the operation of the circuit will change. If the thermostat 122 fails in its open state, then the operator will recognize its failure by the lack of warmth in the contrast medium. The inventive circuit, however, is designed to prevent against overheating of the contrast media, which could be dangerous to the patient. In this regard, it should be noted that thermostat 122 is likely to fail prior to the higher temperature thermostat 124. With thermostat 122 closed at temperatures higher than 98° F, current will continue to flow through heater element 126. However, when the threshold temperature of thermostat 124 is reached, 108° F, then thermostat 124 will open. At this occurrence, and with thermostat 122 closed, current will flow through lamp 128 and be seen by the operator as a glowing pressure jacket. The operator will then know to immediately exchange the heater sleeve 116 for another. Accordingly, with the circuit illustrated in FIG. 7, a malfunction in the heater unit can be sensed prior to overheating the contrast media. In this regard, it should be noted that while the threshold temperature of thermostat 124 is set at 108° F, the contrast media will not reach such a high temperature.

The status indicating circuit will now be described, with reference made to FIG. 8. A lamp 130 will be visible at the panel of control unit 14. Lamp 130 can take three states, the first being off, the second being flashing, and the third being on full. When off, lamp 130 indicates that the injector is not ready for an injection. When flashing, lamp 130 indicates that the injector is in readiness for an injection, and when on full, lamp 130 indicates than an injection is in progress. A continuously running clock 132 issues a train of uniformly spaced pulses. The output from the clock 132 reaches line 134 when the contact of switch 136 is in its relaxed position as illustrated in FIG. 8. When the operator desires to arm the injector circuitry, after the injection parameters are set, button 138 is depressed. Depressing the button 138 results in the issuance of a signal by flip-flop circuit 140, such signal closing a normally open switch 142. With switch 142 closed, the pulses from clock 132 reach the base of a transistor 144, bringing transistor 144 to conduction with the occurrence of each clock pulse. With transistor 144 conductive, the positive potential appearing at terminal 146 passes through the lamp 130 and into ground through transistor 144. With transistor 144 switching from its conductive to its non-conductive states, lamp 130 blinks on and off. In the event that the operator fails to set all of the parameters necessary for a complete injection, then a signal is issued at disarm terminal 148 permitting switch 142 to remain in its normally open position. With switch 142 open, transistor 144 is non-conductive, and no current passes through lamp 130. Accordingly, lamp 130 remains off.

After the operator has set all of the necessary parameters for an injection, and has armed the circuit by depressing button 138, status lamp 130 will blink as described above. Then, when ready to inject, the operator will depress an injection button (not shown) and the injection process will begin. During injection switch 136 will switch from clock 132 to a source of positive potential at terminal 154. With switches 136 and 142 in respective positions other than shown in FIG. 8, the source of positive potential at terminal 154 reaches the base of transistor 134 and maintains the transistor in its conductive state. Conduction of transistor 144 enables the positive potential at terminal 146 to continually flow through status lamp 130. Accordingly, during injection, lamp 130 remains illuminated.

The load control circuit will now be described, referring to FIG. 9. The switch illustrated in FIG. 9 at 22 is the same switch as that illustrated in FIG. 6 at the top of head portion 12. While it should be appreciated that switch 22 is a two-way, forward-reverse switch, it is illustrated in FIG. 9 and is a simple, on-off switch for ease of description. Furthermore, the motor 150 illustrated in FIG. 9 is the same motor as that which actuates the driving mechanism 60 (FIG. 3) for performing an injection operation.

Switch 22 associates with a source of positive potential through terminal 156. In series with the switch 22 is a resistor 158 and a capacitor 160. The potential across capacitor 160 is received and amplified by an amplifier 162, which, in turn, controls the operation of motor 150.

If the switch 22 is held depressed, then capacitor 160 charges to its limit by way of the potential at terminal 156, passing through resistor 158. The voltage across capacitor 160 rises exponentially, as illustrated in FIG. 9 at 164. This signal is amplified by amplifier 152, and results in motor 150 rapidly attaining a high speed, such as is desirable during certain syringe filling operations. If the switch 22, on the other hand, is pulsed, then capacitor 160 is cyclically discharged when switch 22 returns to its ground connection, as is illustrated at 166. Under these conditions, the signal reaching motor 150 through amplifier 162 is at a lesser potential, and hence the motor 150 runs more slowly. Accordingly, with a single switch, it is possible to regulate the speed of motor 150 as is desired.

FIG. 10 illustrates the inventive circuitry for alerting the operator that there is insufficient contrast media in the syringe to complete the required injection. The desired flow of contrast media into the vascular system is programmed into the control unit 14 at volume module 38. Internally, a wiper 168 moves across a variable resistor 170, thereby affecting the signal reaching the non-inverting input terminal of a comparator 172. The other terminal of comparator 172 receives a signal from a variable resistor 174, the wiper 176 of which moves with the plunger 70 which drives the piston of the syringe cartridge. Accordingly, the comparator 172 receives one signal which is directly proportional to the position of the plunger 70, and hence the amount of contrast media remaining in the syringe, and one signal which is proportional to the amount of fluid called for by the operator.

With the output of comparator 172 negative, that is, when there is more fluid than is necessary for an injection, diode 178 blocks the passage of current. However, when the amount of fluid in the syringe is insufficient to meet the demands of the operator, then the output of comparator 172 is positive and this positive signal is passed through diode 178 to each both an indicator lamp 180 and a disarm output 182. In order to prevent the issuance of a disarm signal during an injection which began with sufficient contrast media in the syringe, the start button which initiates the injection is coupled to a switch 184. Therefore, if there is initially sufficient fluid to complete an injection, the commencement of the injection procedure will open switch 184 and hence prevent the issuance of a disarming signal.

While the function of the circuit illustrated in FIG. 10 is to indicate when there is insufficient fluid to carry out an injection, this circuit could be used to determine the volume of contrast media in the syringe. The position of wiper 176 of potentiometer 174 is directly dependent upon the volume of contrast media in the syringe. If the operator wishes to determine this volume, he need only call for more and more fluid by changing the setting on variable resistor 170, until the lamp 180 becomes illuminated. At this instant, the reading on the front panel relative to resistor 170 is an indication of the volume of fluid in the syringe.

Figure 11:
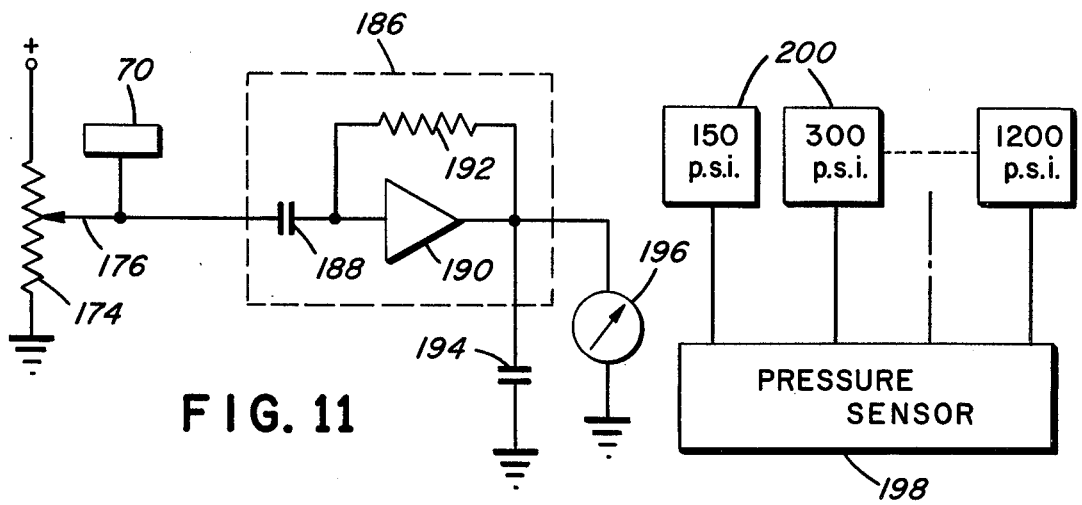
FIG. 11 is a schematic of the flow rate indicator circuit utilized in the inventive injector.

The flow rate indicator circuit is illustrated in FIG. 11. A signal of positive potential is taken from potentiometer 174 by wiper 176. This signal is delivered to a differentiator 186 comprising a capacitor 188 in series with an amplifier 190 having resistance feedback 192. A capacitor 194 stores the peak voltage experienced at the output of the differentiator 186, and this stored peak voltage is reflected at a meter 196.

At the same time that meter 196 indicates the differentiated position signal, or flow rate, an independent circuit is storing pressure information. In this regard, also illustrated in FIG. 11 is an independent pressure sensor network 198 which energizes a set of indicator lamps 200 as their respective threshold pressures are sensed. Accordingly, at the end of an injection operation, meter 196 indicates the maximum flow rate obtained, while indicators 200 represent the maximum pressure attained. With such flow rate and pressure information, the operator is able to make a judgment as to the validity of the injection operation.

Figure 12:
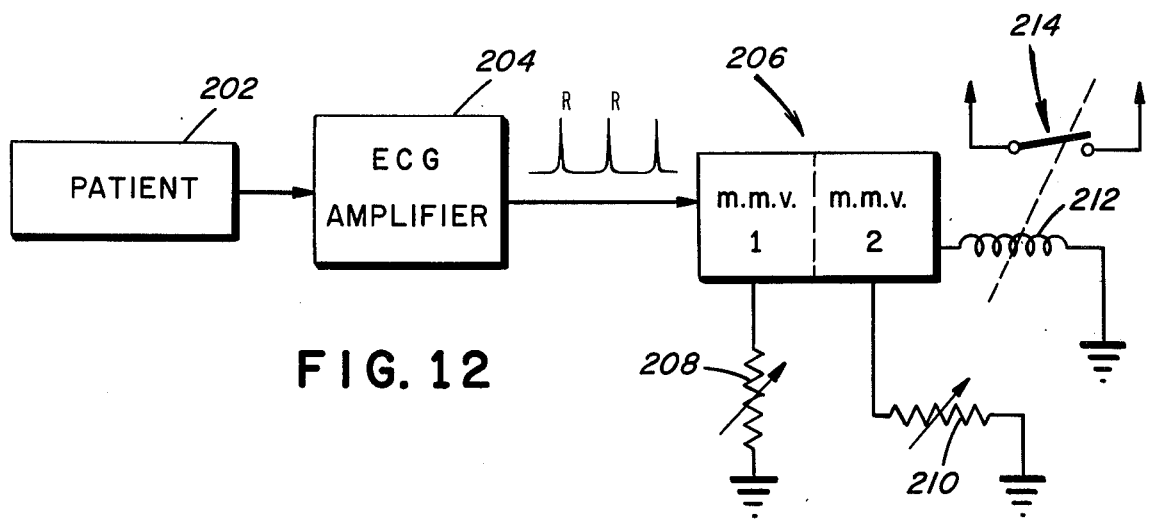
FIG. 12 is a schematic of the delayed ECG trigger circuit.

In FIG. 12, there is illustrated a block diagram of a circuit for closing a switch to external equipment in synchronization with R-waves. A patient 202 is monitored by ECG equipment, and an ECG amplifier 204 generates pulses which correspond to the appearance of R-waves. The pulses generated by amplifier 204 are fed to a monostable multivibrator 206. Multivibrator 206 comprising two series-connected multivibrators, is provided with an adjustable delay resistor 208 and an adjustable duration resistor 210. The setting of delay resistor 208 determines the delay between the initiation of an R-wave and the initiation of a multivibrator signal. Duration resistor 210 determines the width of the multivibrator output pulse. The output from the multivibrator energizes a coil 212 which, in turn, closes a switch shown generally at 214; this switch triggers any output equipment such as a film changer, which is connected thereto.

Figure 13:
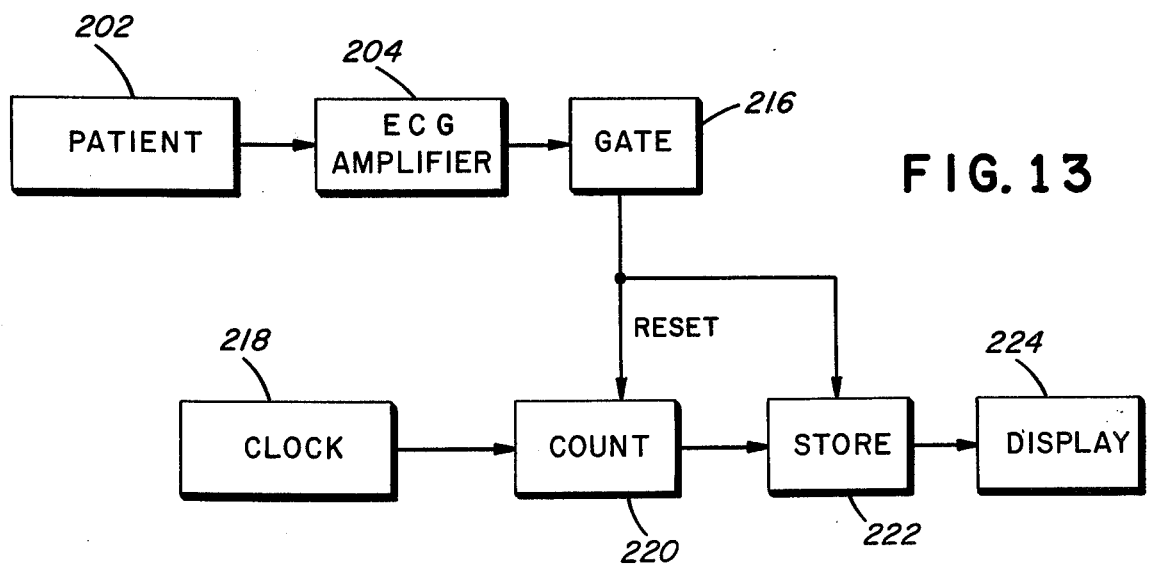
FIG. 13 is a circuit schematic of the R-to-R interval display employed in the inventive injector.

The circuit for displaying the R-to-R interval is illustrated in FIG. 13. There, the R-wave related pulses generated by the amplifier 204 are fed to a gate 216. At the same time, a continuously running clock 218 issues a train of evenly spaced pulses, serving as input signals to a counter 220. The number of clock pulses counted by counter 220 is fed to a storage device 22, which, in turn, feeds information to a display 224 on the panel of the control unit 14. With each R-wave related pulse generated by the amplifier 204, gate 216 issues a signal which resets counter 220 to zero and which instructs the storage circuit 222 to transmit information to the display unit 224, preferably giving a direct reading of the R-to-R interval in hundreths of a second. If desired, a buffer network can be employed ahead of the display circuit 224, so that the interval readings can be averaged.

Figure 14:
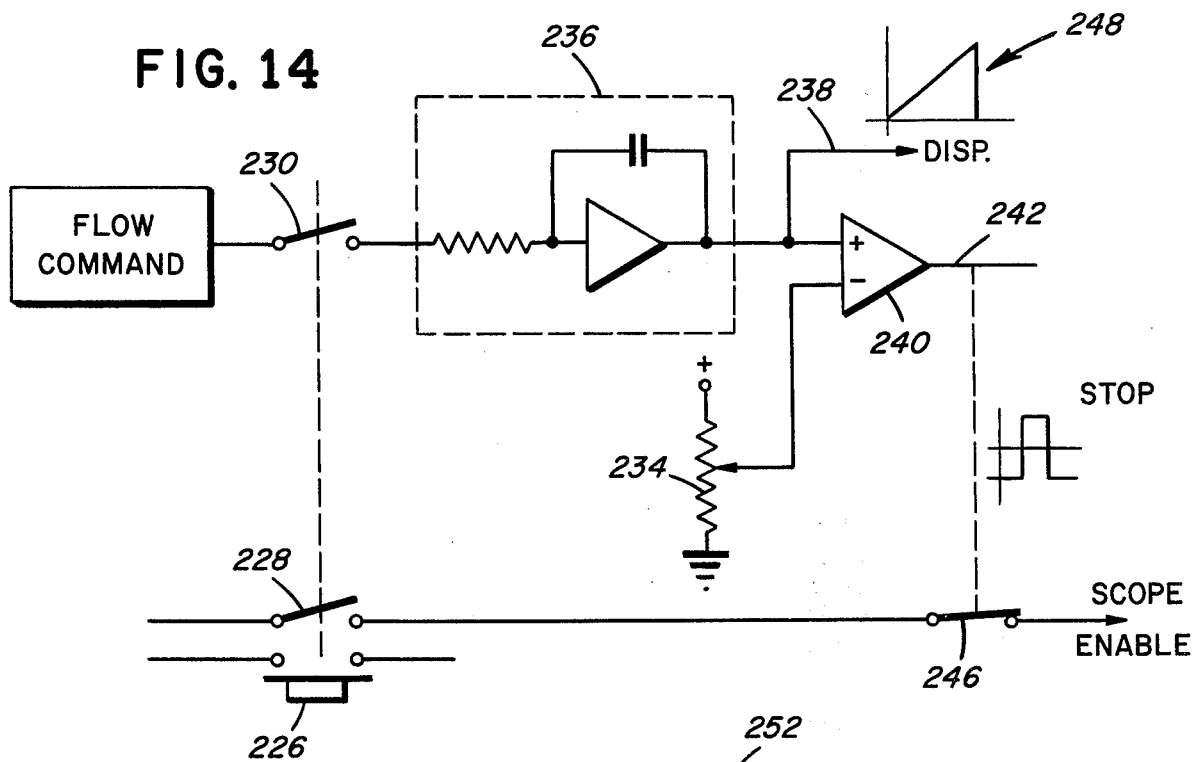
FIG. 14 is a circuit schematic of the program preview forming a part of the inventive injector.

With reference now to FIG. 14, the program preview circuit will be described. The operator actuates this circuit by pressing preview button 226, which is ganged together with a normally open start switch 228 and a normally open power switch 230. Upon closure of switch 228, the horizontal sweep of the oscilloscope is enabled. At the same time, a signal proportional to the flow command is applied to integrator 236. The flow command is integrated by way of integrator 236, and is fed to the oscilloscope via line 238. The output of the integrator 236 is also delivered to the non-inverting input of comparator 240, the inverting input of which receives a signal from the volume setting resistor 234. When the integrated flow signal exceeds the volume signal, the output of comparator 240 goes positive, and a "stop" signal is issued at 242. This signal opens switch 246 and disarms the oscilloscope. The scope trace generated by the signal on line 238 is indicated generally at 248.

Figure 15:
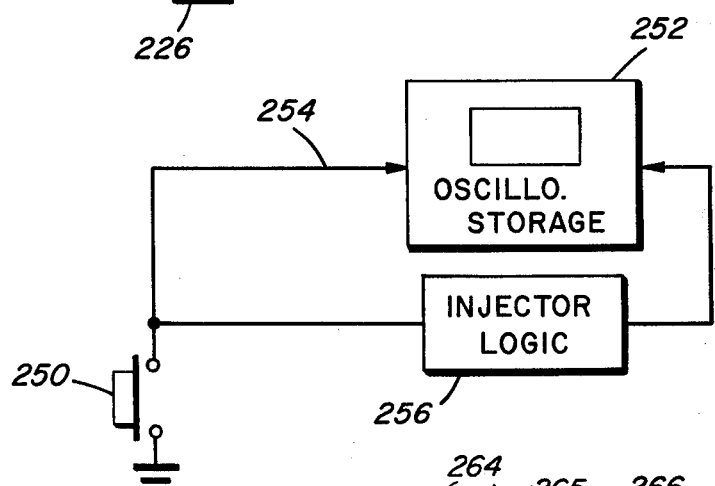
FIG. 15 is a block diagram of the storage oscilloscope for reviewing an actual injection.

The circuit of FIG. 15 is employed to store an injection as it occurs. When the operator depresses the start button 250, the horizontal sweep of the oscilloscope 252 is actuated by a signal delivered along line 254. An injector logic circuit 256, set to begin on the second R-wave, feeds injection information to the oscilloscope 252, and issues a stop command to the oscilloscope upon completion of the injection.

Figure 16:
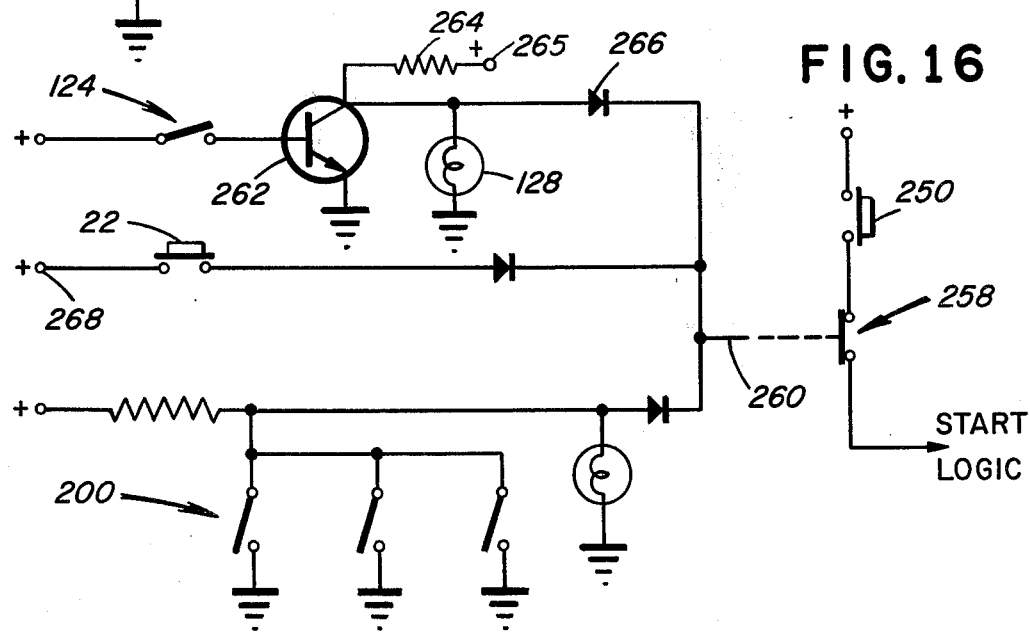
FIG. 16 is a circuit schematic illustrating the automatic disarm feature of the present invention.

FIG. 16 illustrates the automatic disarm circuit utilized in the inventive injector. When the operator is ready to initiate an injection, he depresses the start button 250. If he has taken all preliminary steps required to satisfy the injector circuitry, normally closed switch 258 will indeed be closed, and the start logic will be actuated. However, if the operator has neglected to perform a necessary step in the arming operation, then a disarm signal will be emitted at line 260, and will open switch 258. FIG. 16 is simplified, and is given merely for purposes of illustration. It will be recalled that the opening of thermostat 124 is indicative of a failure in the power circuit. In this regard, when thermostat 124 is closed, transistor 262 conducts, thereby shunting current through resistor 264 to ground. With thermostat switch 124 open, however, the potential at terminal 265 is reflected at lamp 128 and on line 260 via diode 266. When this occurs, switch 258 is opened, thereby disarming the injector circuit. On the other hand, if the operator is manipulating switch 22 on the top of the head portion 12, then a circuit is closed and the potential at terminal 268 is reflected on line 260, thereby disarming the circuit. Similarly, should operator fail to indicate a desired pressure by depressing a pressure switch 200, a lamp will become illuminated and a disarm signal will be issued.

Figure 17:
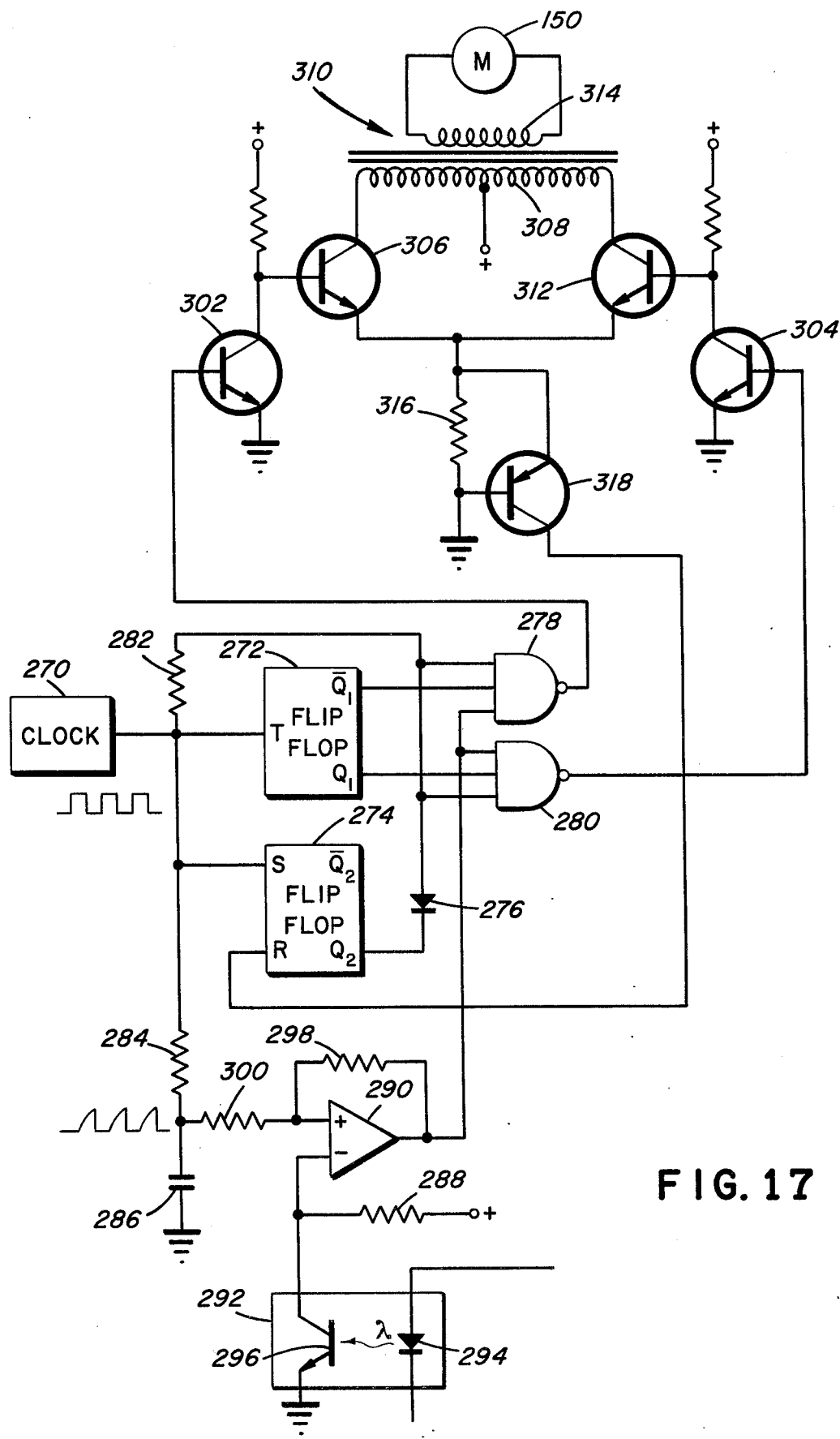
FIG. 17 is a schematic of the inventive motor drive circuit used in the present injector.

Referring now to FIG. 17, the inventive motor drive circuit will be described. A free running clock 270 toggles flip-flop 272, alternately shifting Q1 and Q1 high and low. Once a second flip-flop 274 is set its output Q2 remains high, since there is no reset signal. Therefore, diode 276 has no effect on the clock pulses into gates 278 and 280 through resistor 282. Clock pulses through resistor 284 charge capacitor 286, generating a sawtooth-shaped waveform. A positive voltage is applied through resistor 288 to the inverting input of comparator 290, maintaining the comparator output low.

The desired motor speed is set into optical coupler 292 and controls light-emitting diode 294 to turn on a phototransistor 296 while achieving isolation between the drive signal and the control circuit. As the phototransistor turns on, the threshold on the inverting input of comparator 290 is lowered. If any point on the sawtooth waveform exceeds the threshold set by coupler 292, the output of comparator 290 will flip high. Hysteresis is determined by resistors 298 and 300. This assures that comparator 290 flips quickly when its threshold is exceeded.

The output pulse width of comparator 290 is varied by controlling the threshold on its inverting input. If a high rate drive is applied to coupler 292, the threshold on comparator 290 will be low, and its output will flip high for most of the sawtooth waveform. If a low drive is applied to coupler 292, the threshold on comparator 290 will be high, and its output will flip high only for a small portion of the sawtooth waveform. The pulse width of the comparator output is applied to gates 278 and 280 and determines the width of the drive to transistors 302 and 304.

With Q1 high, two of the three inputs to gate 278 will be high when the clock pulse is high. When the output of comparator 290 goes high, the output of gate 278 will switch low, turning off transistor 302 and allowing transistor 306 to turn on. The output of gate 278 will stay low for the duration set by the output of comparator 290. When the comparator output flips low, the output of gate 278 will return high to turn on transistor 302 and shunt base drive from transistor 306, de-energizing the primary 308 of transformer 310.

With the next clock pulse, Q1 will go high and Q1 low. Now the output of gate 280 will be controlled by the pulse width of the comparator output. When the output of comparator 290 goes high, the output of gate 280 goes low, turning off transistor 304 and allowing transistor 312 to turn on. The side of primary 308 connected to transistor 312 will now be energized. The output of gate 280 will stay low for the duration set by the comparator output. When the output of comparator 290 flips low, the output of gate 280 will return high to turn on transistor 304 and shunt base drive from transistor 312, de-energizing primary 308.

The power transferred to the secondary 314 is proportional to the amount of alternating current flowing through the primary over a period of time. Current through the primary 308 develops voltage across resistor 316 proportional to instantaneous current. If the current through the resistor is sufficient to turn on transistor 318, flip-flop 274 will be reset by the collector voltage of transistor 318. When flip-flop 274 resets, output Q2 will go low. Clock pulses through resistor 282 will be shunted through diode 276. This shuts off any drive to transistors 302 and 304 until the next clock pulse, which sets flip-flop 274 and flips output Q2 high. Series resistor 316 is selected to turn on transistor 318 when current through the primary 308 exceeds the maximum useful level. This prevents saturating the transformer and possibly damaging transistors 306 and 312.

It will be noted that if one of the drive transistors fails in a closed state, direct current will flow in the primary 308 of tansformer 310, and hence no current will flow in the secondary 314 to energize motor 150. Accordingly, the motor 150 is protected against overheating by virtue of a failure in its control circuitry.

Figure 18:
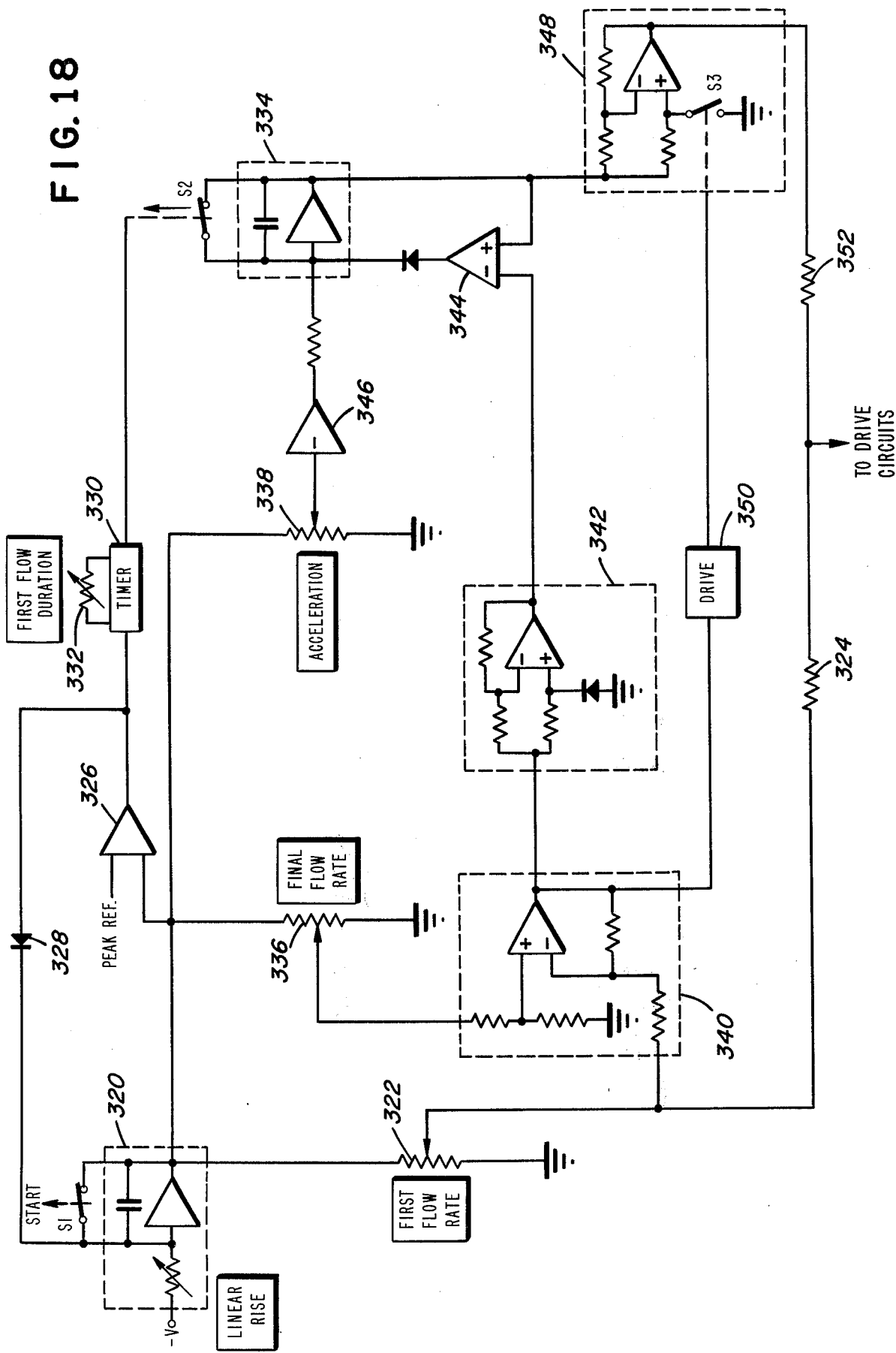
FIG. 18 is a circuit schematic of the inventive four-mode variable injection rate programmer.

Referring now to FIG. 18, the inventive four-mode variable rate injection circuit will be described. When the start command is given, S1 opens, allowing the integrator 320 to generate a positive ramp. A portion of the ramp and the plateau is selected by resistor 322, proportional to desired first flow rate, and fed out resistor 324 as the flow command, to drive the main flow circuit.

When the output of integrator 320 achieves the peak reference to the threshold detector 326, the detector output (through diode 328), clamps the integrator 320 at the reference level detector 326. Simultaneously, timer 330 being timing. The timer duration is set by resistor 332. When the time interval has elapsed, S2 opens and integrator 334 is enabled.

As noted above, after the linear rise duration, when the output of integrator 320 achieves the peak reference, the output will be clamped at the peak. This peak is also used by resistors 336 and 338 to select, respectively, final flow rate and acceleration.

A subtraction circuit 340 compares the settings of resistors 322 and 336. Specifically, the first flow rate, set by resistor 322, is subtracted from the final flow rate set by resistor 336. The output of circuit 340 may either be positive or negative, negative if the final is lower than the first flow rate.

The drive circuit 350 responds only to negative signals. closing S3 with a negative output from subtraction circut 340. The significance of this closing will be described below.

An absolute value circuit 342 processes the output of subtraction circuit 340 such that the output of the absolute value circuit 342 is always positive by the difference between the first and final flow rates. This absolute value is used by a comparator 344. The absolute value serves as a reference, determining how far the integrator 334 must charge to get from one level to another.

It will be recalled that integrator 334 remains at rest until the timer 330 opens S2. When S2 opens, integrator 334 begins integrating at the rate set by resistor 338. The setting of resistor 338 must be inverted by an inverter 346 so that the integrator 334 will have a positive output. The integrator 334 will continue charging unti its output becomes elevated to the reference level into comparator 344 from absolute value circuit 342. When integrator 334 has integrated this desired increment, comparator 344 clamps the output by balancing the input. The integrator's output will then hold at the level achieved when the comparator 344 was triggered. The integrator 334 will have charged by the increment determined by circuit 340 subtracting the first from the final flow rate.

The integrator 334 always integrates positive. This is no problem if the final flow rate is set higher than the first flow rate. However, if the final flow rate is set lower than the first, there should be negative acceleration. Circuit 346 inverts positive acceleration when the final flow rate is less than the first flow rate.

If acceleration should be positive, S3 stays open, giving a gain of +1 to a polarity determining circuit 348. Positive acceleration feeds right through. But if a negative difference is detected by the drive circuit 350, S3 is closed to cause circuit 348 to have a gain of −1, inverting the positive acceleration ramp.

The signals at the junction of resistors 324 and 352 will add. If the output of circuit 348 is negative, it will subtract from the level on resistor 322 to cause the junction voltage to lower from the original value. Of course, if the output of circuit 348 rises positively, the composite will increase from the original level to the final level.

The junction of resistors 324 and 352 represents the flow command. This will control the main flow circuit to drive the motor according to the generated waveform.

With this circuit, an unlimited number of flow curves can be achieved. The flow can first accelerate, and then drop to zero, remain constant, accelerate again, or perhaps decelerate. The rates of acceleration can also be varied over a wide range of possibilities. Accordingly, this circuit can be put to wide use in special purpose injection operations.

Figure 19:
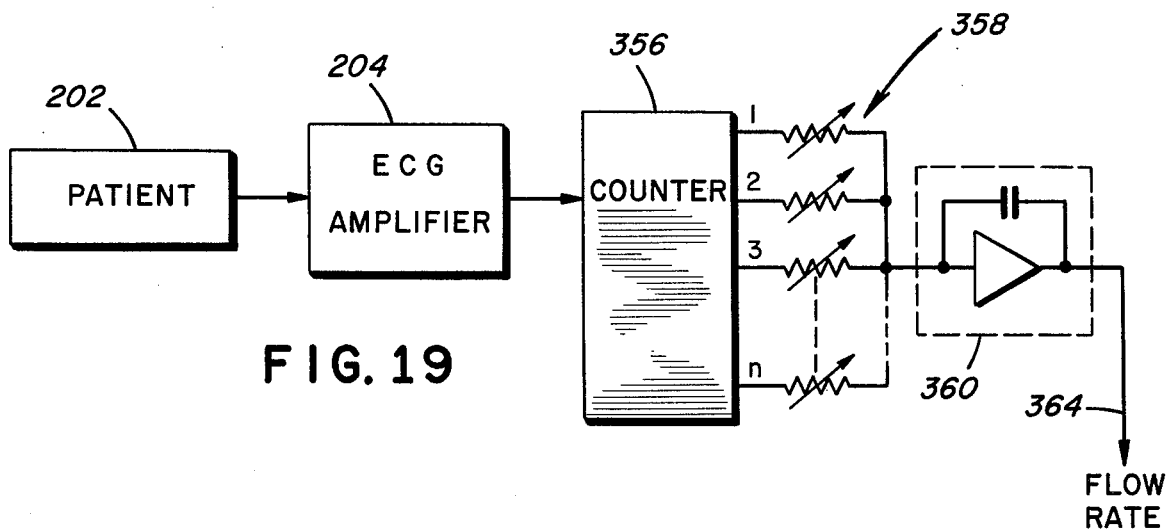
FIG. 19 is a schematic ECG advance circuit.

With reference now to FIG. 19, the sequential ECG advance circuit will be described. As noted above, this circuit yields the capability of delivering injections on successive R-waves, with the flow rate of each injection being adjustable. The patient is shown in FIG. 19 at 202, and an ECG amplifier can be seen at 204. As will be recalled, the ECG amplifier develops pulses which correspond in time with the R-waves generated by the patient 202. The output from the ECG amplfer 204 is fed to a counter circuit 356 having a plurality of outputs, each one of which associates with a variable resistor 358. The sides of the resistors 358 remote from the counter 356 are united and associate with an integrator 360. The output of integrator 360 is taken at 364 and is a flow rate control signal.

In operation, the resistors 358 are initially set by manipulating corresponding controls on the front of the control unit panel in accordance with the desired injection profile. Then, once set, the circuit of FIG. 19 is actuated, and the counter 356 is zeroed. At the first R-wave related pulse generated by ECG amplifier 204, counter 356 causes a signal to be developed across resistor 358 on line 1. The signal across resistor 358 on line 1 is reflected at output 364, and a first injection is initiated in accordance with this first flow rate signal. At the occurrence of the second pulse from ECG amplifer 204, counter 356 actuates the resistor 358 on line 2, and a second flow rate signal is developed on line 364. It will be noted that resistors 358 are able to map out substantially any given injection profile, each injection of which correlates with the occurrence of an R-wave.

Figure 20:
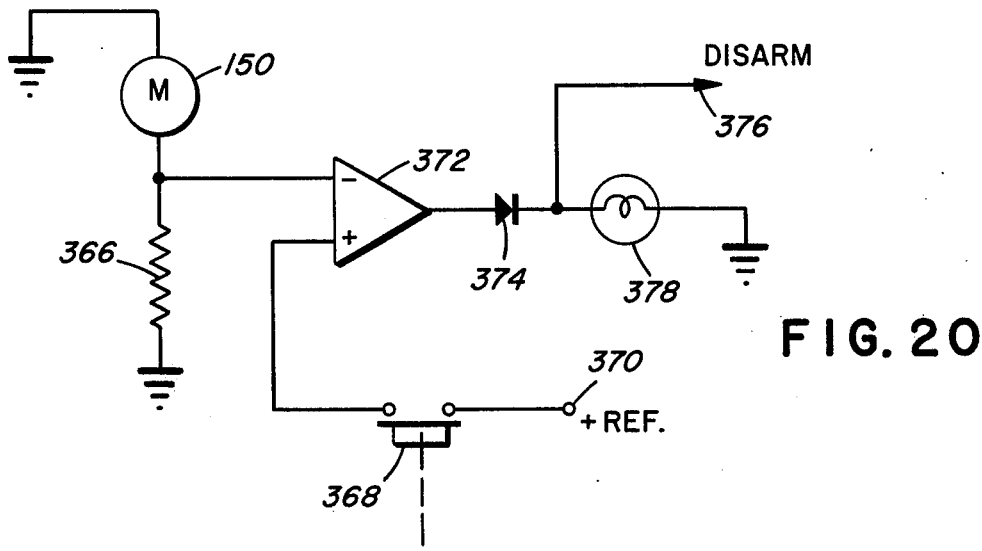
FIG. 20 is a schematic of a circuit for detecting the presence of air in the syringe cartridge by monitoring motor current.

FIG. 20 illistrates a first circuit for recognizing the presence of air in a syringe prior to the initiation of an injection cycle. This circuit recognizes air as a function of current drain by the motor 150 through resistor 366. When the start button to initiate an injection is depressed, switch 368 closes. Accordingly, a pre-set reference voltage appearing at junction 370 is delivered to the non-inverting input of comparator 372. A signal proportional to the current through the motor 150 and resistor 366 is impressed at the inverting input of comparator 372. Just so long as the signal developed by the voltage at junction 370 is less than the signal developed in porportion to the current through motor 150, a diode 374 blocks any output of comparator 372. However, if the current signal should fall below that developed by the reference potential, then the comparator output 372 flips over and a signal is generated at disarm output 376. At the same time, lamp 378 is illuminated. Under conditions when the syringe is filled with fluid, the current drain from motor 150 will be high. However, when the syringe is partly filled with air, this air can easily be compressed by the pressures generated by motor 150, and hence current drain will be reduced. This reduced current drain is detected by the circuit of FIG. 20.

Figure 21:
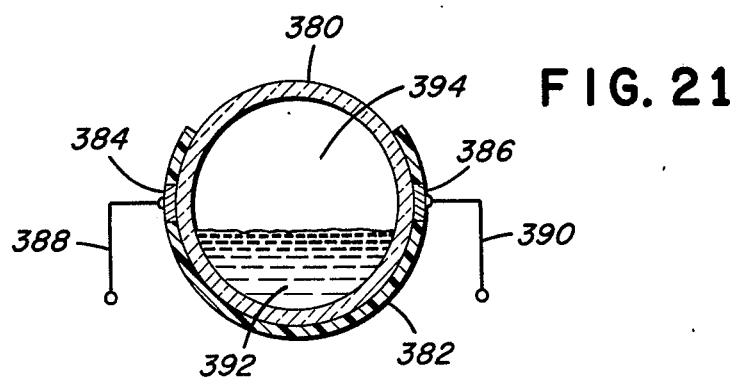
FIG. 21 is a schematic of an alternate configuration for detecting air in the syringe, utilizing a characteristic of the syringe-fluid combination.

In FIG. 21, there is illustrated another embodiment for detecting air in the syringe. A syringe cartridge is shown at 380 and has a detector strap 382 associated therewith. Strap 382 houses detector elements 384 and 386 which associate, respectively, with electrical leads 388 and 390. Contrast media is shown at 392, and air is shown in the syringe 380 at 394. In the embodiment illustrated in FIG. 21, detector elements 384 and 386 can take the form of capacitor plates which sense the electrical capacity through the contrast media. The capacity will be different from a full condition to one in which air is present. Or, on the other hand, element 384 may take the form of a light emitting diode, and 386 the form of a phototransistor. Again, light transmitting characteristics will change depending upon whether the syringe is filled with contrast media 392, or has an amount of air 394 present. If air is detected by way of the elements 384 and 386, then a disarm signal can be generated and a lamp illuminated similar to the manner which is illustrated in FIG. 20.

Figure 22:
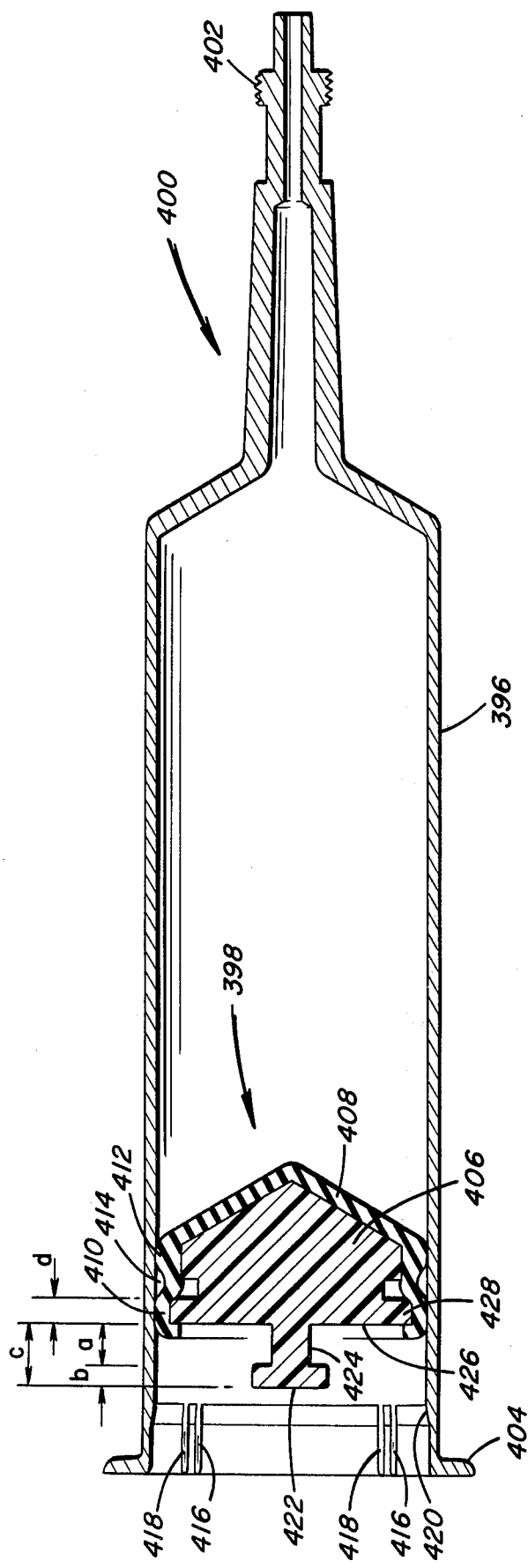
FIG. 22 is a cross section through a syringe cartridge adapted to associate with the inventive angiographic injector.
Figure 23:
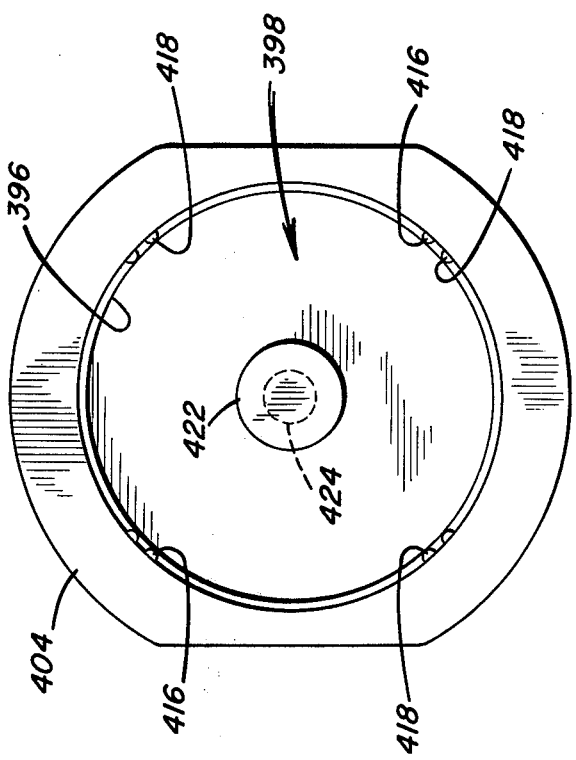
FIG. 23 is an end view of the syringe shown in FIG. 22.

A syringe is illustrated in FIGS. 22 and 23. The syringe jacket is shown at 396, and the associated plunger at 398. At the forward end of the jacket 396 is a tip 400 which extends through the forward end of the pressure jacket on the turret assembly. The tip 400 is threaded at 402 for connection of an appropriate catheter. At the rear portion of the syringe jacket 396 is a flange 404 which serves as an abutment face for associating with the rear portion of the pressure jacket on the turret assembly. The plunger 398 comprises a plastic base member 406 having a rubber sheath 408 thereover. The rubber sheath defines two annular seals designated in FIG. 22 at 410 and 412.

It is desirable to sterilize the syringe assembly with the plunger 398 positioned within the jacket 396. A problem has existed, however, in that the space 414 between the annular seals 410 and 412 has been impervious to sterilizing gas. Accordingly, impurities have tended to be a problem. With the inventive syringe, sterilizing gas is able to enter the space 414 between seals 410 and 412. In this regard, the rearwardmost portion of jacket 396 is provided with internal irregularities in the form of ridges 416 and 418. In this manner, when the rearwardmost seal 410 associates with ridges 416 and 418, sterilizing gas can seep into the space 414, hence curing the prior art problems with respect to contamination. The inventive syringe is also equipped with a bevel surface 420 at the rearward portion thereof, so that the rubber sheath 408 is not damaged when inserted into the jacket 396.

It should be recalled that when discussing FIG. 4, it was noted that dimensions on the clip 64 were critical. These dimensions given with respect to FIG. 4 are adapted to match corresponding dimensions of a button 422 at the rear surface of plunger 398. As best seen in FIG. 22, the button 422 is connected to the rearward surface of plunger body 406 through the means of a stem 424.

With reference both of FIGS. 4 and 22, the association of the syringe plunger 398 with the plunger 70 of the injector will be described. If the plunger 398 is in a position illustrated in FIG. 22, then there will not be immediate mating between the clips 62 and 64 and the plunger 398. Rather, when the syringe 396 is positioned within the pressure jacket and turret 28 rotated into operative position, the plunger 70 of the injector must be moved forwardly in order to capture plunger 398. In this regard, sloping surface 74 on the forward face of clip 64, and the associating surface on clip 62 are cammed over the button 422 as the plunger 70 is moved forwardly. Once the button 422 is in alignment with the opening 84 in clip 64 and the corresponding opening in clip 62, then the clips snap over and capture the button 422. At this time, ram sections 66 and 68 will contact the rear face 426 of plunger body 406. It will be noted in FIG. 4 that when the rams 66 amd 68 contact surface 426, the button 422 is held out of contact with clips 62 and 64. Otherwise, the clips would fail under injection pressures. During an injection, the ram portions 66 and 68 control the operation of the plunger 398. At the end of an injection, the clips 62 and 64 retract the plunger 398 through the means of button 422.

If the plunger 398 is at the extreme rearward end of jacket 396, with the button 422 extending out of the jacket, then the sloping faces 76 and 78 of the clips 62 and 64 come into play. Under these conditions, the clips are cammed by the button 422 as the turret 28 is rotated. In all other respects, the operation of the injection and retraction modes are the same.

In order to minimize stresses in the clips 62 and 64, and in the button and stem 422 and 424, respectively, it has been necessary to carefully dimension the button, stem, and spacings illustrated in FIG. 4. In this regard, it has been found that excellent results are obtained with a stem length $a$ somewhere between 0.185 and 0.255 inches, with a button length $b$ being 0.09 inches. Said another way, it has been found appropriate to dimension the button and stem combination such that the total length $c$ is somewhere between 0.185 and 0.350 inches. A preferable stem dimension $a$ is 0.220 inches.

It can be seen in FIG. 22 that the body 406 of plunger 398 comprises two cylindrical regions, the rearward region of which is designated 428. It has been found that especially with small volume syringes, such as 65 ml syringes, width $d$ of this region is important. In this regard, to eliminate the possibility of the region 428 snapping off of the syringe during an injection, the width $d$ of body 406 should be at least 0.20 inches.

Figure 24:
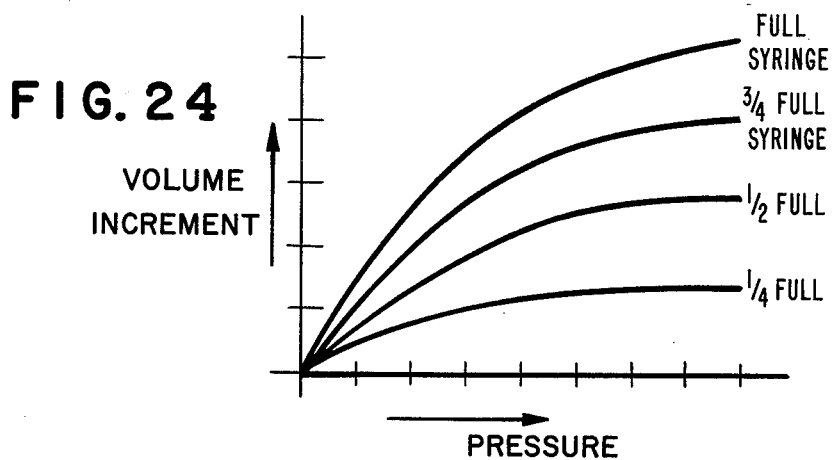
FIG. 24 is a graph showing the effects of pressure and media volume on changes of syringe capacity.
Figure 25:
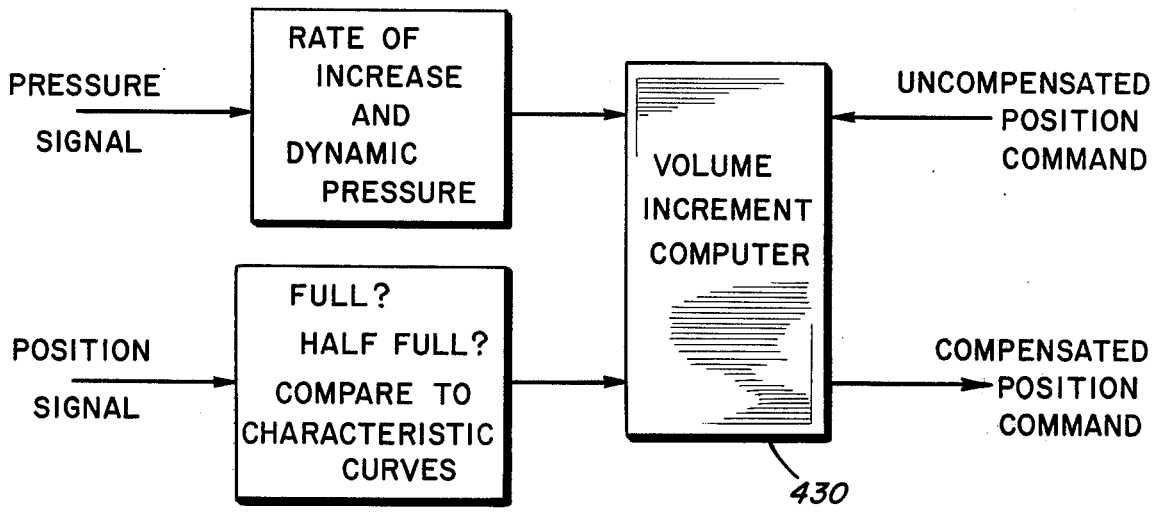
FIG. 25 is a block diagram of the capacity compensating circuit forming a part of the present invention.

Referring now to FIGS. 24 and 25, the circuitry for compensating for capacity changes in the syringe assembly during injection operations will be described. As previously noted, due to expansion of the syrings and pressure jacket, compression of the cover on the plunger, and stretching of the syringe/pressure jacket assembly and mounting means, there may be considerable time between the start command (given by the injector's drive circuits) and the point at which full flow and pressure are developed in the catheter. Actual catheter flow, considering the effects of changes in capacitance, takes the form of a long, gradual increase in rate. Media will be wasted. Furthermore, this long, sloppy rise time is undesireable in EGG-synchronized injections of multiple boluses. In such an appliation, flow rate must rise quickly to enable sharp contrast.

The effects of changes in capacitance in a syringe system may be seen in the graph of FIG. 24. The vertical scale is marked in volume increments of overall capacity change, the increment of volume utilized before pressure is fully developed at the syringe tip. It can be seen that the increment of capacity change varies with the amount of media in the syringe (position of the plunger relative to syringe length) and the delivery pressure. Generally, change in capacity increases proportional to the distance between the plunger and syringe tip, and change in capacity increases proportional to pressure.

The compensation network illustrated in FIG. 25 utilizes both pressure and position to arrive at a volume increment to compensate for capacity changes.

In FIG. 25, the pressure input to the compensation network could take the form of a signal proportional to the torque developed by the driving motor 150. The position input can take the form of a signal derived from the potentiometer 174 associated with the plunger 70. The position command is derived from the flow control signal and fed into the volume increment computer 430. The output of the volume increment computer is then fed back to the original connection input to the flow control signal, to add or subtract therefrom.

Pressure is monitored for two purposes. If pressure is increasing rapidly (particularly during start-up), this may be interpreted as the system expanding due to a change in capacity. And the actual pressure should be known to compare against the characteristic curves shown in FIG. 24. The position of the plunger sets the range of compensation, determining which of the characteristic curves of FIG. 24 should be plotted to add an increment to the position command.

The volume increment computer 430 senses the pressure and position signals to process a compensated position command signal for the main flow circuit. As pressure builds up, a volume increment will be added to the position command to cause a burst of power to the motor. The expansion characteristics will have been pre-programmed into the volume increment computer so that the volume increment will vary according to actual pressure and position. Volume increment will vary with position such that higher increments will be given with the plunger close to the syringe heel.

With such a compensating circuit, it is possible to obtain rapid rise times for injection flow by over-driving the motor during initial stages of drive, and it is also possible to eliminate the effects of continued flow due to capacity changes after pressure is removed. The resultant catheter flow becomes more square with capacitance compensation. Flow rate with minimal rise time gives excellent contrast in cardiac viewing with a minimum bolus volume. Contrast media will not be wasted, and opacity will simply be a function of flow rate, media, and the catheter.

Figure 26:
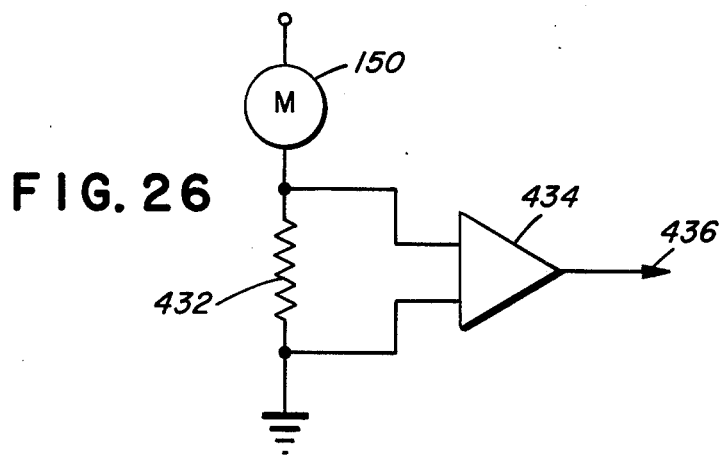
FIG. 26 is a circuit schematic illustrating the pressure read-out provided in the inventive injector.

In FIG. 26, the pressure read-out circuit will be described. As noted with respect to FIG. 25, a torque signal is used as the pressure signal input. This torque signal is developed by the circuit of FIG. 26. In this FIG., motor 150, when operating, draws a certain amount of current and hence develops a given voltage across a resistor 432. The current drawn by motor 150 is proportional to the torque developed by this motor. An amplifier 434 detects the signal across resistor 432, and issues an amplified output at line 436. This output at line 436 is therefore also proportional to the torque developed by motor 150.

With reference now to FIG. 27, the overall block diagram of the inventive angiographic injector will be described. The controls from control unit 14 appear along the left edge of FIG. 27. The blocks represent functional circuit groups within the system. The injector head 12 is shown on the right side with its components and controls.

The timer circuit 438 gives the signals to inject when the operator presses the hand switch 440. A film changer may by synchronized with the start of an injection, as set by the operator.

The volume circuit 442 monitors the position of plunger 70 after an injection begins to determine how much volume of contrast media has been delivered. And when the plunger has delivered the set volume, the volume circuit 442 sends a signal to the timer circuit 438 to stop injecting.

The arm circuit 444 ensures that a number of prerequisites are met, then allows the operator to arm the injector. When the injector is armed a signal will be given to the timer 438 to enable an injection to begin. The arm circuit 444 also enables the safe relay to close in the power amplifier 446 for forward motion of the motor.

The flow command generator 448 uses the settings of the operator's flow controls to generate a flow command, a voltage waveform proportional to the desired flow magnitude and linear rise time.

The main flow circuit 450 uses the flow command and various other inputs to generate a rate error drive to propel the motor 150. The main flow circuit 450 is also responsive to the load signal from the load circuit 452 to move the plunger 70 at a controlled rate for loading.

The pressure circuit 454 uses the motor current as an indication of pressure, reading out this pressure on the bank of pressure monitor lights 456. The pressure circuit also allows pressure to be limited to a value set by the pressure limit pushbuttons 456. If the actual pressure attempts to exceed the set limit, the pressure circuit 454 will send a signal to the main flow circuit 450 to limit power.

The system monitor circuit 458 monitors two conditions. First, it continuously monitors the integrity of the potentiometer 174 connections between the injector head 12 and the control unit 14. Since the system relies on the potentiometer's signal for processing into actual rate and position, it is vital that the connections be maintained. If the signal drifts beyond pre-selected limits, a signal will be given to the arm circuit 444 to prevent an injection until integrity is restored. Secondly, the plunger's rate is monitored during an injection. If the actual rate exceeds the set flow rate by a significant amount, the system monitor circuit 458 will give a signal to the arm circuit 444 to stop the injection.

When the load buttons are depressed, the load circuit 452 causes the necessary events to occur to enable controlled loading.

The power amplifier circuit 446 controls power to the motor 150 to drive the plunger 70 at the desired flow rate.

The injector head 12 houses only a limited number of controls, the load button 22 for forward/reverse loading and the armed light 130 which indicates status. Switches 462 in the head 12 enable an injection only when the rotating double syringe assembly 28 and mechanical stop are in positions ready for injection. The motor 150 and potentiometer 174 are mechanically connected together and to the plunger 70. As the motor 150 drives the plunger 70, the potentiometer 174 tracks it, so that rate of movement and position may be derived. Finally, the heater 126, a self-contained unit, maintains media temperature in the syringe. A dual thermostat circuit protects the heater 126 from overheating, and gives visual indication if the primary thermostat fails.

The overall system concept is that the control unit 14 sets the desired magnitudes and durations of injection parameters, the injector head 12 attempts to follow the set parameters, and feeds information back to the control unit 14 to compensate for variables.

With reference now to FIGS. 28a and 28b, a mechanism for limiting the travel of the plunger 70 will be described. The limiting mechanism is shown generally at 500 and is set by actuation of the same lever 516 as is illustrated in FIGS. 1 and 6. Integral with lever 516, but positioned inside the casing of head 12, is a hub 502. A band 504, as of metal, is fixed to the surface of hub 502 by way of a bolt, the head of which can be seen at 506.

The end of band 504 remote from hub 502 is connected to take-up reel 508 rotatably mounted on a shaft 510. A solid abutment block 512, as of metal, is fixed to the band 504 intermediate hub 502 and reel 508, through the means of a bolt 514.

As seen best in FIG. 28a, hub 502 is integral with a rotating clutch 518 having teeth 520 around its periphery. A fixed clutch 522 is coaxially mounted with respect to rotating clutch 518, and has peripheral teeth 524 adapted to mesh with corresponding teeth 520 of cluth 518. Fixed clutch 522 is mounted for linear axial movement as represented by arrow 526, and is permitted a small degree of angular rotation. Movement of clutch 522 in the direction of arrow 528 results in engagement with clutch 518. Movement in the opposite axial direction disengages clutches 522 and 518. A pin 528 is mounted on the surface of fixed clutch 522, and is adapted to actuate a microswitch 530 through control arm 532. While not shown in FIG. 28a, rotation of knob 26 illustrated in FIGS. 1 and 6 moves the fixed clutch 522 in the axial direction indicated by arrow 526 to engage or disengage clutches 522 and 518.

A rigid follower block 534 is mounted for linear movement in the directions indicated by arrow 536. Block 534 is guided by a shaft 538 which passes through a bore 540 in the lower region of the block. A pair of guiding arms 542 and 544 extend from block 534 and associate with band 504 in such a manner that ban 504 is held between arms 542 and 544. Arm 542, as best seen in FIG. 28a, aligns with block 512 so that movement of follower block 534 in the direction of abutment block 512 can continue only until arm 542 contacts a stop face 546 on block 512.

The operation of the limiting mechanism 500 is as follows. When the operator wishes to begin an injection, the knob 26 is rotated so as to disengage clutches 518 and 522. Then lever 516 is actuated, moving block 512 to the desired position, indicated at the scale 20 shown in FIGS. 1 and 6. The lever 516 is moved until the scale 20 indicates the desired injection volume. Then knob 26 is turned, locking clutches 518 and 522. The injection is initiated, and the plunger 70 (FIG. 4) forces contrast media from the associated syringe. As plunger 70 moves, so too does follower block 534, as indicated in FIG. 28b. Then, upon completion of an injection, follower block 534 contacts abutment block 512 through arm 542. This contact results in the above-noted slight rotational movement permitted fixed clutch 522, and microswitch 530 is actuated by pin 528 contacting control arm 532. Actuation of microswitch 530 disenables the motor driving the plunger 70, and hence interrupts further injection. Therefore, if the electrical shut-off circuitry should fail, an injection will still be timely concluded by operation of the limiting mechanism 500.

Above, there have been described the specific embodiments of the inventive angiographic injector and syringe. It should be appreciated that this description is given for purposes of illustration only, and is intended in no way to limit the scope of the present invention. Rather, it is the intention that the present invention be limited only as defined in the appended claims.

We claim:

1. An apparatus for injecting a contrast media into the vascular system of an animal, the apparatus comprising: a head porton means for supporting a plurality of cartridges housing contrast media and provided with a motor means to drive the contrast media out of said cartridges; and a control unit means; said head portion comprising a rotating turret for housing at least two syringe cartridges in readiness for injection.

2. The apparatus recited in claim 1, wherein said rotating turret includes an elongated base rotatably mounted at its center; and wherein a syringe cartridge is housed at each end of said elongated base.

3. The apparatus recited in claim 2, and further comprising alignment means at each end of said elongated base for aligning the respective syringe cartridges on said head portion in predetermined positions prior to injections.

4. The apparatus recited in claim 2, and further comprising spring contact means on said head portion movable by said motor and for associating with the respective syringe cartridges; wherein each syringe cartridge includes a plunger for driving contrast media out of said syringe, and a button connected to said plunger by a reduced diameter shaft, said button adapted to associate with said spring contact means.

5. The apparatus recited in claim 4, wherein said spring contact means comprise first and second associated spring clips spaced apart by a distance less than the diameter of said button, wherein said spring clips are adapted to be cammed apart by said button when said turret is rotated or when said motor is actuated, and wherein said spring clips are adapted to retract said plunger upon actuation of said motor in a retracting sense.

6. The apparatus recited in claim 2, and further comprising switch means for preventing operation of said motor unless said turret is in a predetermined orientation on said head portion.

7. An apparatus for injecting contrast media into the vascular system of an animal, the apparatus comprising holding means for a media containing syringe, means for forcing media from said syringe and into said vascular system, and including a media-warming heater comprising: a heating element; first and second thermostats connected in series with said heating element, the respective thermostats designed to operate at a first temperature and at a second and higher temperature, each being normally closed and opening at the respective first and second temperatures; means for connecting a source of electrical energy to the series circuit of said heating element and said first and second thermostats; and means for indicating failure of said first thermostat to open at said first temperature.

8. The apparatus recited in claim 7, wherein said first thermostat is designed to open at on the order of 98° F, and wherein said second thermostat is designed to open at on the order of 108° F.

9. The apparatus recited in claim 8, wherein said means for indicating failure comprises a lamp connected in parallel to said second thermostat, and wherein said lamp becomes illuminated by said source of electrical energy upon the opening of said second thermostat.

10. An apparatus for injecting a contrast media into the vascular system of an animal said apparatus comprising: holding means for a media-containing syringe; means for forcing media from said syringe and into said vascular system; means for controlling the injection of contrast media into said vascular system; means for programming the injection of contrast media into the vascular system; and an indicator for representing the state of said apparatus, said indicator comprising illuminator means, circuit means for disabling said illuminator means if the apparatus is not in readiness to inject contrast media, for flashing said illuminator means when said apparatus is armed, and for maintaining said illuminator means in an illuminated condition when said apparatus is injecting contrast media.

11. An apparatus for injecting contrast media into an animal and comprising: holding means for a media-containing syringe; means for forcing media from said syringe and into said vascular system; programming means for setting the amount of contrast media desired for injection and for programming said apparatus for injecting such desired amount of contrast media; means for sensing the actual amount of contrast media in a syringe associated with said apparatus and in readiness to inject contrast media into the animal; and indicator means for indicating a condition wherein the sensed contents of contrast media in the syringe is less than that programmed by said programming means.

12. An apparatus for injecting contrast media into an animal and comprising: holding means for a media-containing syringe; means for preselecting and delivering the contrast media to the animal at a pre-set injection rate; means for recording the highest flow-rate attained during the injection and for maintaining an indication of such flow-rate; and means for sensing and recording the highest pressure attained during said injection and for maintaining an indication of such pressure.

13. An apparatus for injecting a contrast media into the vascular system of an animal, the apparatus comprising: a main casing holding on said main casing means for a media-containing syringe; means for forcing media from said syringe into said vascular system; means mounted in proximity to said main casing for sensing the actual cardiac R-waves of an animal; means for generating signals representative of the actual cardiac R-waves of said animal; output means for operating an external device in synchronism with said R-waves upon the closure of an output circuit; and means for closing said output circuit in synchronism with said signals for actuating said external device.

14. The apparatus of claim 13, wherein said output circuit is closed for a predetermined interval, and at a predetermined delay after the occurrence of each R-wave.

15. The apparatus of claim 13, wherein the injection of contrast media is permanently recorded on film; and wherein said external device is a film changer apparatus.

16. An apparatus for injecting a contrast media into an animal, wherein means are provided for programming the injection of the contrast media in accordance with a desired flow pattern, and comprising: a main casing holding means on said main casing for a media-containing syringe; means for forcing media from said syringe into said vascular system; means mounted in proximity to said main casing for sensing the actual cardiac R-waves of the animal; means for developing signals representative of the time spacing between successive R-waves; means for displaying the recorded interval between successive R-waves; and means for programming the injection of contrast media into said animal at a rate and volume so as to confine said injection to an R-to-R interval time pattern.

17. An apparatus for injecting contrast media into an animal, the apparatus comprising: a main casing; holding means on said main casing for supporting at least one media-containing syringe; means mounted in proximity to said main casing for sensing and displaying ECG information of the animal; means for forcing contrast media out of a media-containing syringe and into an animal; means for setting the desired flow-rate for the injection of contrast media into the animal and for injecting the contrast media into the animal at said flow-rate; means for setting the desired volume of contrast media to be injected into the animal and for injecting said volume of contrast media into the animal; and display means for previewing the flow and volume settings, the ECG information and the manner in which the flow and volume injection of contrast media synchronizes with said ECG information prior to the initiation of an injection so that the necessity for flow or volume setting adjustments can be previewed prior to actual injection.

18. The apparatus recited in claim 17, wherein said display means is an oscilloscope.

19. An apparatus for injecting a contrast media into an animal, the apparatus comprising: holding means for receiving a media-containing syringe; means for forcing contrast media from said syringe into said animal; sensor means for associating with said syringe and for sensing the presence of contrast media and air in said syringe; and indicator alarm means for indicating the presence of air and issuing an alarm signal upon such presence of air.

20. The apparatus recited in claim 19, wherein said sensor means includes a motor for controlling the ejection of contrast media into said animal; and further comprising means for sensing the current drain on said motor during an injection; and threshold means for actuating said indicator alarm means upon said current drain falling below a predetermined threshold.

21. The apparatus of claim 19, wherein said sensor means comprises a light emitting diode and a photoresistor spaced apart and on opposite sides of said syringe; and further comprising means for actuating said diode; means for monitoring said photoresistor; and means for actuating said indicator alarm upon the response of said photoresistor to the light emitted by said diode falling outside of predetermined threshold limits.

22. The apparatus recited in claim 19, wherein said sensor means comprises first and second capacitor plates spaced apart and on opposite sides of said syringe; and further comprising means for sensing the capacity between said first and second capacitor plates; and means for actuating said indicator alarm upon said capacity falling outside predetermined threshold limits.

23. An apparatus for injecting contrast media into an animal, the apparatus comprising: housing means for receiving and supporting a media-containing syringe; ejector means including a drive motor for forcing contrast media out of said syringe and into said animal in accordance with a pre-determined program; means for sensing the volume of contrast media in said syringe prior to the commencement of the injection; and means for over-driving said drive motor at the beginning of the injection and in accordance with a program which is proportional to the desired pressure of injection and the volume of contrast media sensed in said syringe prior to the commencement of the injection.

24. An apparatus for injecting a contrast media into an animal wherein a plunger forces a contrast media out of a syringe, and including a mechanism for preventing the plunger from excessive travel, the apparatus comprising: mounting means for supporting a media-containing syringe having a plunger to force contrast media therefrom; mechanical actuating means for controlling the operation of said plunger by linear movement; stop means integral with said actuating means, movable therewith and hence with said plunger; a movable abutment surface adapted to associate with said stop means for limiting the movement of said actuating means and hence said plunger; and means to move said abutment surface into preselected positions wherein said stop means contacts said abutment surface at locations corresponding to plunger positions where the desired amount of contrast media is injected.

25. The apparatus recited in claim 24, wherein said abutment surface is mounted on a movable band.

26. The apparatus recited in claim 25, wherein one end of said movable band is mounted on a rotatable clutch hub, and wherein said abutment surface is moved by rotating said clutch hub about a central axis thereof.

27. The apparatus recited in claim 26, and further comprising a fixed clutch hub for associating with said rotatable clutch hub, and further comprising means for engaging and disengaging said rotatable clutch hub from said fixed clutch hub.

28. An apparatus for injecting contrast media into the vascular system of an animal, the apparatus comprising: mounting means for accepting a contrast media-filled syringe; ejector means for forcing contrast media out of said syringe and into the animal; means for preselecting a first flow rate, and for controlling said ejector means to eject contrast media from said syringe and into the animal from a zero rate to said first flow rate; first duration means for preselecting the duration of media injection at said first flow rate, and for discontinuing injection at said first flow rate after the preselected duration; means for preselecting a final flow rate and for controlling said ejector means to eject contrast media at said final flow rate; acceleration means for preselecting a desired acceleration or deceleration from said first flow rate to said final flow rate, and for controlling said ejector means to accelerate or decelerate the injection from said first flow rate to said final flow rate; and volume limiting means for discontinuing the ejection of contrast media into the animal upon the ejection of a preselected volume of contrast media.

29. The apparatus recited in claim 28, and further comprising rise time means for adjusting the time duration between the commencement of an injection and the attainment of said first flow rate.

30. The apparatus recited in claim 28, and including means for controlling said ejection means so that the acceleration from zero to said first flow rate is linear.

31. An apparatus for injecting contrast media into an animal, the apparatus comprising: housing means for receiving and supporting a media-containing syringe; ejector means including a drive motor for forcing contrast media out of said syringe and into said animal in accordance with a pre-determined program; and means for over-driving said drive motor at the beginning of the injection so as to initially develop an injection pressure higher than the pre-programmed initial pressure of injection.

* * * * *